(12) United States Patent
Takato

(10) Patent No.: US 10,914,935 B2
(45) Date of Patent: Feb. 9, 2021

(54) OBJECTIVE OPTICAL SYSTEM

(71) Applicant: OLYMPUS CORPORATION, Hachioji (JP)

(72) Inventor: Hideyasu Takato, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 99 days.

(21) Appl. No.: 16/192,304

(22) Filed: Nov. 15, 2018

(65) Prior Publication Data

US 2019/0086658 A1    Mar. 21, 2019

Related U.S. Application Data

(63) Continuation of application No. PCT/JP2017/014122, filed on Apr. 4, 2017.

(30) Foreign Application Priority Data

May 16, 2016 (JP) .................. 2016-098172

(51) Int. Cl.
  *G02B 23/24* (2006.01)
  *G02B 23/26* (2006.01)
  *G02B 13/04* (2006.01)
  *A61B 1/00* (2006.01)
  *G02B 15/173* (2006.01)

(52) U.S. Cl.
  CPC ...... *G02B 23/2438* (2013.01); *A61B 1/00096* (2013.01); *A61B 1/00188* (2013.01);
  (Continued)

(58) Field of Classification Search
  CPC .... G02B 15/173; G02B 15/177; G02B 15/14; G02B 13/009; G02B 27/646; G02B 15/00;
  (Continued)

(56) References Cited

U.S. PATENT DOCUMENTS 4,312,572 A    1/1982   Yamashita et al.
4,764,001 A    8/1988   Yokota
            (Continued)

FOREIGN PATENT DOCUMENTS

JP     61044283 B2    10/1986
JP     04003851 B2     1/1992
            (Continued)

OTHER PUBLICATIONS

International Search Report (ISR) dated Jul. 4, 2017 issued in International Application No. PCT/JP2017/014122.
(Continued)

*Primary Examiner* — William R Alexander
*Assistant Examiner* — Sharrief I Broome
(74) *Attorney, Agent, or Firm* — Holtz, Holtz & Volek PC

(57) ABSTRACT

The objective optical system includes a first lens group having a positive refractive power, a second lens group having a negative refractive power, and a third lens group having a positive refractive power. Focusing is carried out by moving the second lens group. The third lens group includes a positive lens and a cemented lens, and the cemented lens includes a positive lens and a negative lens. A first sub-unit includes a lens positioned on the object side of a predetermined air space and a second sub-lens group includes a lens positioned on an image side of the predetermined air space. The predetermined air space is the maximum air space among the air spaces in the third lens group.

6 Claims, 11 Drawing Sheets

(52) U.S. Cl.
CPC ........... *G02B 13/04* (2013.01); *G02B 15/173* (2013.01); *G02B 23/26* (2013.01)

(58) Field of Classification Search
CPC ........ G02B 3/14; G02B 3/0081; G02B 7/102; G02B 13/0045; G02B 15/17; G02B 27/0025; G02B 13/18; G02B 26/005; G02B 7/10; G02B 13/04; G02B 13/16; G02B 15/04; G02B 21/22; G02B 27/09; H04N 5/2254; H04N 5/23209; H04N 5/23296; H04N 5/2251; H04N 5/232; H04N 5/23212; H04N 5/238; H04N 13/236; H04N 5/225; H04N 5/23241; H04N 5/77; H04N 5/907; H04N 9/3176; H04N 9/7921; G03B 2205/0046; G03B 17/00; G03B 17/17; G03B 5/00; G03B 13/32; G03B 13/36; G03B 15/00; G03B 17/06; G03B 17/14; G03B 17/54; G03B 19/00; G03B 19/14; G03B 21/005; G03B 21/14; G03B 21/142; G03B 21/28; G03B 2205/0007; G03B 2205/0084; G03B 2217/007; G03B 3/10
See application file for complete search history.

(56) References Cited

U.S. PATENT DOCUMENTS

| | | | |
|---|---|---|---|
| 6,252,723 B1 | 6/2001 | Nagaoka | |
| 6,433,937 B1 | 8/2002 | Konno | |
| 2010/0020408 A1* | 1/2010 | Noguchi | G02B 15/173 359/676 |
| 2010/0142058 A1 | 6/2010 | Takato | |
| 2015/0103418 A1* | 4/2015 | Takato | G02B 23/243 359/754 |
| 2016/0370558 A1* | 12/2016 | Takato | G02B 13/006 |
| 2017/0052359 A1* | 2/2017 | Katakura | A61B 1/06 |

FOREIGN PATENT DOCUMENTS

| | | |
|---|---|---|
| JP | 06317744 A | 11/1994 |
| JP | 11316339 A | 11/1999 |
| JP | 2000267002 A | 9/2000 |
| JP | 3765500 B2 | 4/2006 |
| JP | 2009294496 A | 12/2009 |
| JP | 2012032576 A | 2/2012 |
| JP | 2015121649 A | 7/2015 |
| WO | 2014132494 A1 | 9/2014 |
| WO | 2016006486 A1 | 1/2016 |
| WO | 2016056447 A1 | 4/2016 |

OTHER PUBLICATIONS

Written Opinion dated Jul. 4, 2017 issued in International Application No. PCT/JP2017/014122.

International Preliminary Report on Patentability (IPRP) (and English language translation thereof) and Written Opinion dated Nov. 20, 2018 issued in counterpart International Application No. PCT/JP2017/014122.

\* cited by examiner

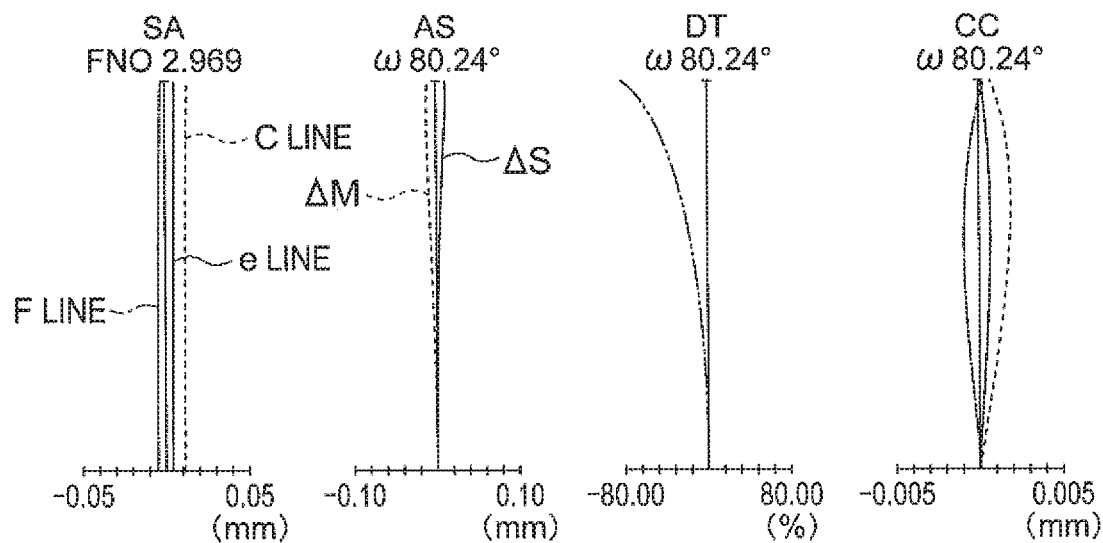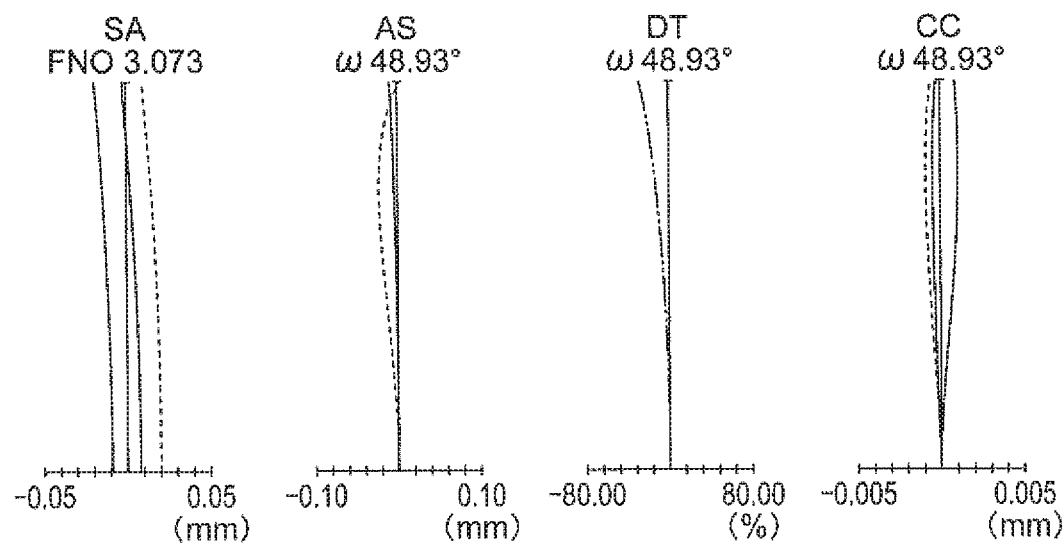

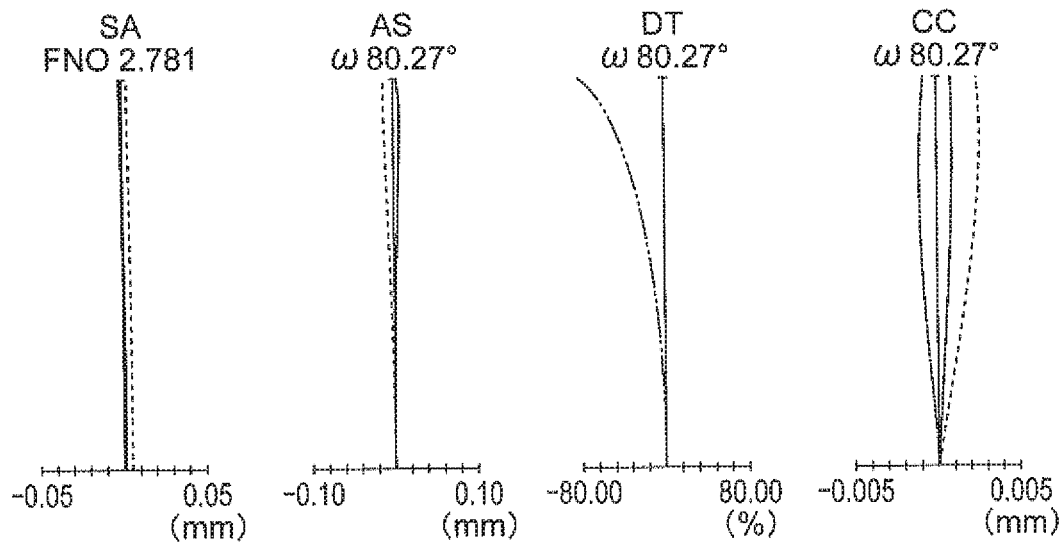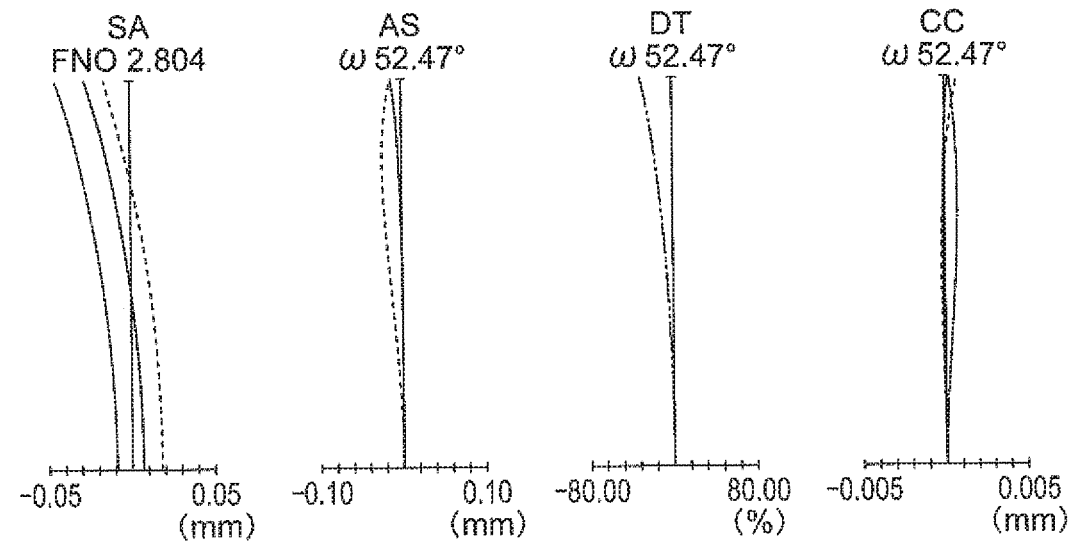

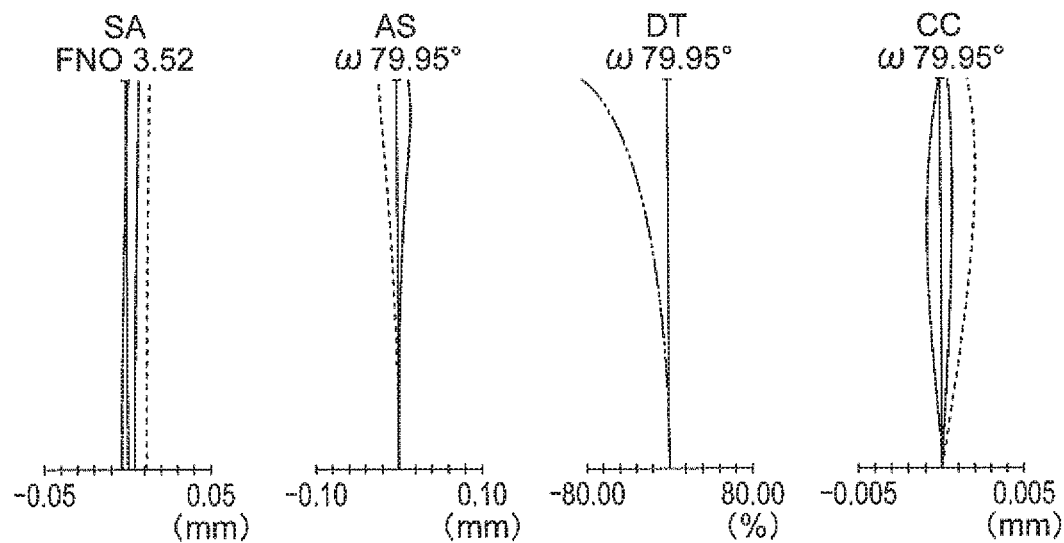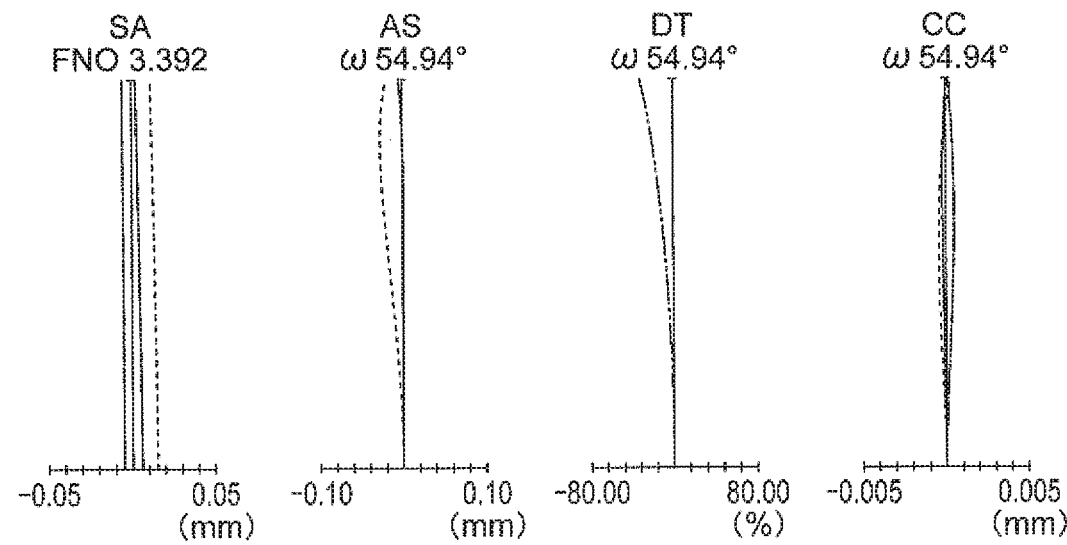

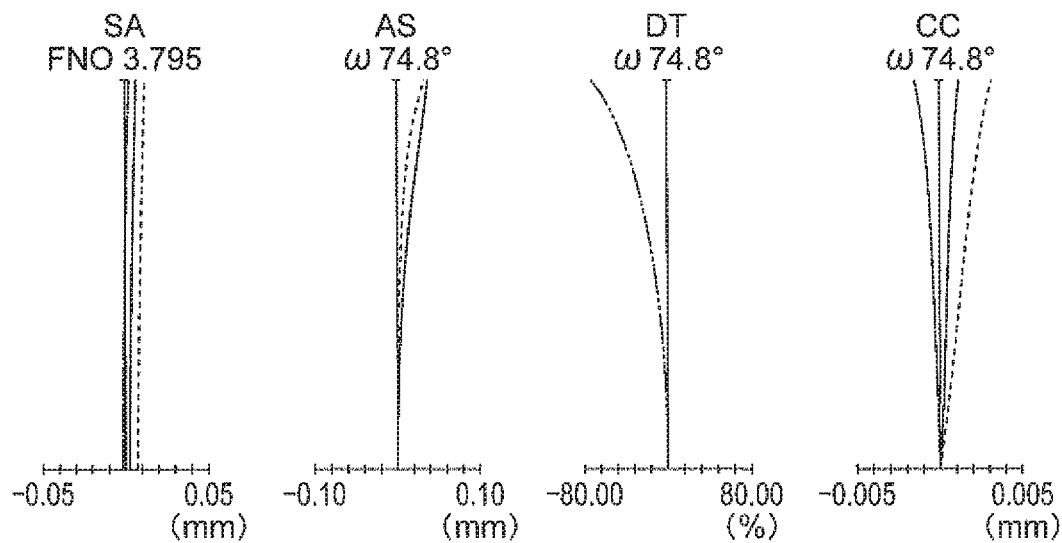
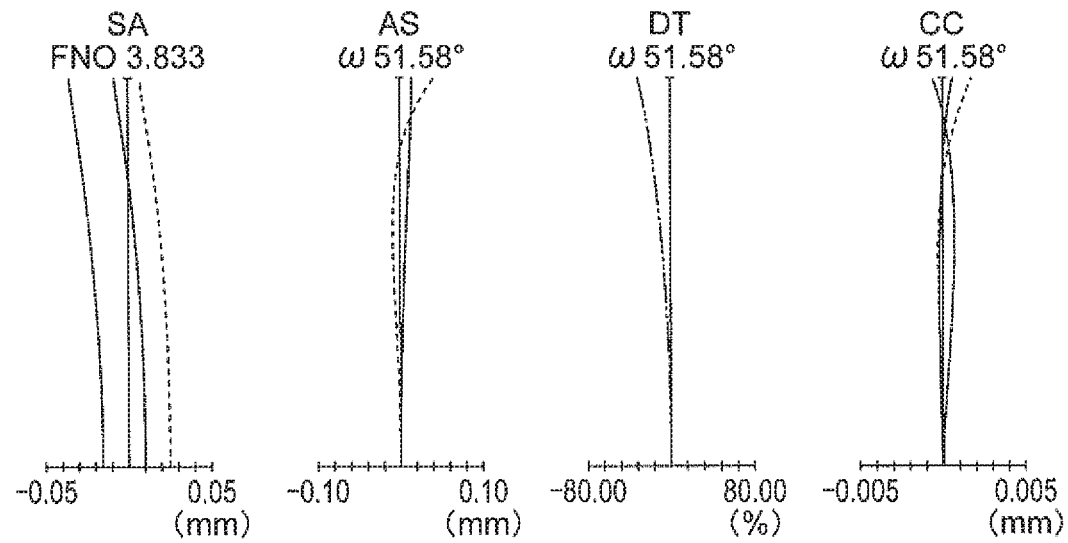

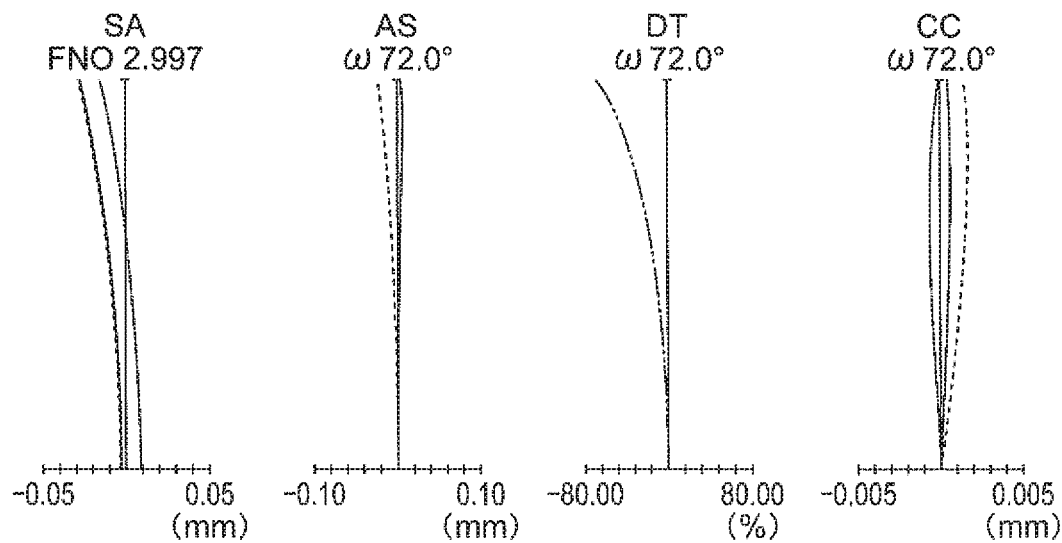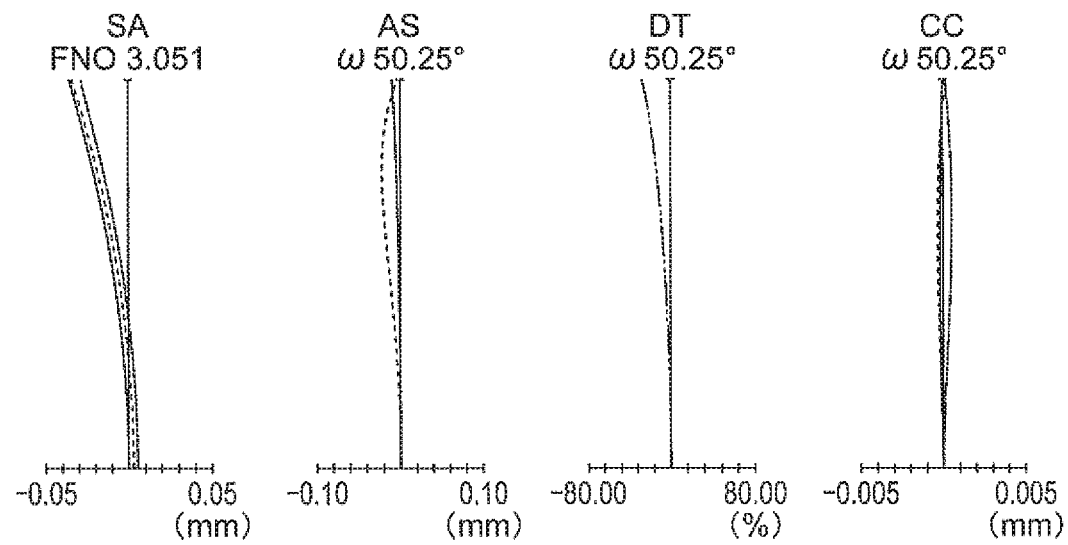

OBJECTIVE OPTICAL SYSTEM

CROSS-REFERENCE TO RELATED APPLICATION

The present application is a continuation application of PCT/JP2017/014122 filed on Apr. 4, 2017, which is based upon and claims the benefit of priority from Japanese Patent Application No. 2016-098172 filed on May 16, 2016; the entire contents of which are incorporated herein by reference.

BACKGROUND OF THE INVENTION

Field of the Invention

The present invention relates to an objective optical system which has a focusing function, and particularly to an endoscope objective optical system which enables a magnified observation, and an objective optical system of other small-size cameras for household use.

Description of the Related Art

An objective lens for commonly-used endoscopes has a wide depth of field. In an objective lens for commonly-used endoscopes, the depth of field is 5 mm to 100 mm for example. In an endoscope having such objective lens mounted, an object image is captured by an image pickup element, and accordingly an image of an object is provided. As an image pickup element, a CCD (Charge Coupled Device) and C-MOS (Complementary Metal Oxide Semiconductor) etc. are used.

In recent years, in a diagnosis using an endoscope, for improving an accuracy of diagnosis, achieving high image quality has been sought. To fulfil this requirement, making number of pixels large has been advancing in an image pickup element. In an image pickup element in which making number of pixels large has advanced, or in other words, in a high-definition image pickup element, an area of a pixel becomes small.

When an image of a point of an object is formed by an objective lens, a point image is formed on an image plane of the objective lens. This point image has a spreading to a certain degree due to an effect of diffraction. Consequently, when the area of a pixel becomes small, if the point image is not made small accordingly, it is not possible to achieve an image of a high image quality even by using a high-definition image pickup element. For making the point image small, it is necessary to make an F-number of the objective lens small.

In a case in which a size of the image pickup element is the same, it is possible to make the number of pixels large by making the area of the pixel small. However, when the number of pixels is made substantially large, even when the size of a pixel is made small, a size of the image pickup element becomes large. When the size of the image pickup element becomes large, it is necessary to make a focal length of the objective lens long.

When the F-number of the objective lens becomes small or when the focal length of the objective lens becomes long, the depth of field of the objective lens becomes narrow. In such manner, when an attempt is made to achieve an image quality higher than the conventional image quality, the depth of field of the objective lens becomes narrow.

The depth of field is a range in which a sharp object image to be achieved, is expressed in a range on an object side. When the depth of field of the objective lens becomes narrow, the range in which a sharp image is achieved becomes narrow. For securing the depth of field of a level same as the conventional level, the objective lens is to be provided with the focusing function. For such reason, the necessity of the objective lens having the focusing function has been increasing.

Moreover, in recent years, in a field of medical endoscopes, a qualitative diagnosis of lesion parts has been carried out. In this diagnosis, the magnified observation of a lesion part becomes necessary. For such reason, in medical endoscopes, the necessity of an objective lens having a magnification function (hereinafter, referred to as 'magnifying endoscope objective lens') has been increasing.

In order to carry out magnified observation of a lesion part, it is necessary to find the lesion part. An observation range being narrow in the magnified observation, it is not easy to find the lesion part by the magnified observation. For such reason, in the magnifying endoscope objective lens, a capability to observe a range wider than the magnified range in the magnified observation becomes necessary.

In the magnified observation, a distance from the objective lens up to an object position (hereinafter, referred to as 'object distance') is about 1 mm to 3 mm. Whereas, in the observation of a wide range as mentioned above (hereinafter, referred to as 'normal observation'), the object distance is much longer than 3 mm.

When an optical system is arranged such that the object position at the time of normal observation and the focal position of the objective lens coincide, an object image in the normal observation (hereinafter, referred to as 'normal image') becomes a focused image.

On the other hand, the object position at the time of magnified observation is away from the object position at the time of normal observation. Moreover, the object position at the time of magnified observation is not included in the depth of field of the objective lens. Consequently, in an optical system in a state in which a normal image is focused, the object image in the magnified observation (hereinafter, referred to as 'magnified image') does not become a focused image.

For achieving a magnified image which is focused even in the magnified observation, the objective lens is to be provided with the focusing function. By the objective lens having the focusing function, it is possible to observe both the normal image and the magnified image in a state of being focused. For such reason, the necessity of the objective lens having the focusing function has been increasing.

As a magnifying endoscope objective lens, objective lenses which include three lens groups have been disclosed in Japanese Patent Publication after Examination No. Sho 61-044283, Japanese Patent Application Laid-open Publication No. Hei 06-317744, Japanese Patent Application Laid-open Publication No. Hei 11-316339, Japanese Patent Application Laid-open Publication No. 2009-294496, Japanese Patent Application Laid-open Publication No. 2012-32576, Japanese Patent Application Laid-open Publication No. 2000-267002, Japanese Patent No. 3765500 Publication, and Japanese Patent Publication after Examination No. Hei 4-3851.

The objective lenses disclosed in Japanese Patent Publication after Examination No. Sho 61-044283, Japanese Patent Application Laid-open Publication No. Hei 06-317744, Japanese Patent Application Laid-open Publication No. Hei 11-316339, Japanese Patent Application Laid-open Publication No. 2009-294496, and Japanese Patent Application Laid-open Publication No. 2012-32576, include in order from an object side, a lens group having a positive refractive power, a lens group having a negative refractive power, and a lens group having a positive refractive power.

The objective lens disclosed in Japanese Patent Application Laid-open Publication No. 2000-267002 includes in order from an object side, a lens group having a negative refractive power, a lens group having a positive refractive power, and a lens group having a negative refractive power.

The objective lenses disclosed in Japanese Patent No. 3765500 Publication and Japanese Patent Publication after Examination No. Hei 4-3851 include in order from an object side, a lens group having a negative refractive power, a lens group having a positive refractive power, and a lens group having a positive refractive power.

In Japanese Patent Publication after Examination No. Hei 4-3851, an objective lens different from the abovementioned objective lenses has been disclosed. The objective lens which is different includes a lens group having a positive refractive power, a lens group having a positive refractive power, and a lens group having a negative refractive power. Still another objective lens includes a lens group having a negative refractive power, a lens group having a negative refractive power, and a lens group having a positive refractive power.

In the objective lenses described in Japanese Patent Publication after Examination No. Sho 61-044282, Japanese Patent Application Laid-open Publication No. Hei 06-317744, Japanese Patent Application Laid-open Publication No. Hei 11-316339, Japanese Patent Application Laid-open Publication No. 2009-294496, and Japanese Patent Application Laid-open Publication No. 2012-32576, focusing to the object at the time of magnified observation is possible. Therefore, in these objective lenses, observation with magnification necessary for carrying out qualitative diagnosis of a lesion part is possible. In the objective lenses disclosed in Japanese Patent Application Laid-open Publication No. 2000-267002, Japanese Patent No. 3765500 Publication, and Japanese Patent Publication after Examination No. Hei 4-3851, a lens is disposed on an image-pickup surface side. This lens is a so-called field lens.

Even in an endoscope which enables magnified observation (hereinafter, referred to as 'magnifying endoscope'), an image pickup element in which the number of pixels is made large has been used. Moreover, in image pickup elements in which the number of pixels is made large, small-sizing has been advancing year by year.

Moreover, in endoscopes, an adjustment of an image position is carried out at the time of assembling. In the adjustment of the image position, an arrangement is to be made such that, at the time of normal observation, the normal image is formed at the image position of the objective lens. An image pickup surface of the image pickup element is positioned at the image position of the objective lens. Therefore, in the adjustment of the image position, adjustments such as an adjustment for moving the overall objective lens or an adjustment for moving some of the lenses in the objective lens is to be carried out such that the normal image is formed on the image pickup surface.

When the conventional objective lens is simply small-sized, a ratio of an amount of movement of the image with respect to an amount of adjustment of the lens at the time of adjustment of the image position (hereinafter, referred to as 'adjustment sensitivity') becomes high.

SUMMARY OF THE INVENTION

An objective optical system according to at least some of the embodiments of the present invention comprises in order from an object side:

a first lens group having a positive refractive power,
a second lens group having a negative refractive power, and
a third lens group having a positive refractive power, wherein
focusing is carried out by moving the second lens group, and
the third lens group includes at least a positive lens and a cemented lens, and
the cemented lens in the third lens group includes a positive lens and a negative lens, and
a first sub-lens group in the third lens group includes a lens positioned on the object side of a predetermined air space, and
a second sub-lens group in the third lens group includes a lens positioned on an image side of the predetermined air space, and
the predetermined air space is the maximum air space among the air spaces in the third lens group, and
the following conditional expressions (1) and (2) are satisfied:

$$1.21 < fp/f < 2.42 \quad (1), \text{and}$$

$$0.35 < tt/f < 0.6 \quad (2)$$

where,
fp denotes a combined focal length from the first lens group up to the first sub-lens group,
f denotes a focal length of the overall objective optical system at the time of focusing to an object point at a long distance, and
tt denotes the predetermined air space.

BRIEF DESCRIPTION OF THE DRAWINGS

FIG. 3A, FIG. 3B, FIG. 3C, FIG. 3D, FIG. 3E, FIG. 3F, FIG. 3G, and FIG. 3H are aberration diagrams of the objective optical system of the example 1;

FIG. 5A, FIG. 5B, FIG. 5C, FIG. 5D, FIG. 5E, FIG. 5F, FIG. 5G, and FIG. 5H are aberration diagrams of the objective optical system of the example 2;

FIG. 7A, FIG. 7B, FIG. 7C, FIG. 7D, FIG. 7E, FIG. 7F, FIG. 7G, and FIG. 7H are aberration diagrams of the objective optical system of the example 3;

FIG. 9A, FIG. 9B, FIG. 9C, FIG. 9D, FIG. 9E, FIG. 9F, FIG. 9G, and FIG. 9H are aberration diagrams of the objective optical system of the example 4;

FIG. 11A, FIG. 11B, FIG. 11C, FIG. 11D, FIG. 11E, FIG. 11F, FIG. 11G, and FIG. 11H are aberration diagrams of the objective optical system of the example 5.

DETAILED DESCRIPTION OF THE INVENTION

Figure 1A:
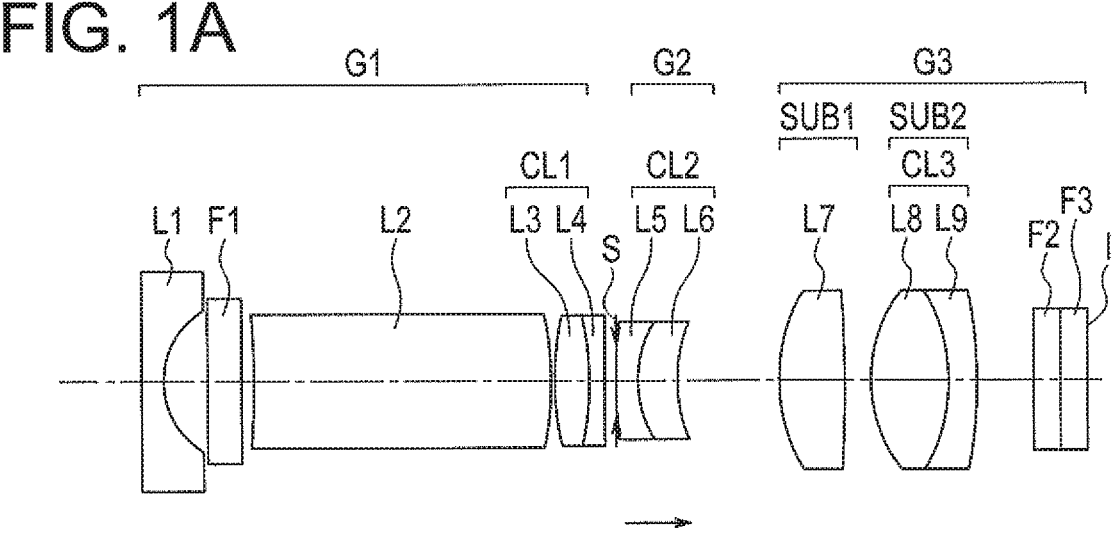
FIG. 1A and FIG. 1B are cross-sectional views showing a specific arrangement of an objective optical system of the present embodiment.

Reasons for adopting such arrangements and effects thereof in an objective optical system according to the present embodiment, will be described below by referring to the accompanying diagrams. However, the present invention is not restricted to the objective optical system according to the following embodiment.

It is possible to use an objective optical system according to the present embodiment for an objective lens of an endoscope for example. In this case, the objective optical system according to the present embodiment, in an endoscopic observation, enables to carry out a normal observation and a magnified observation with one optical system. For this, the objective optical system is formed by a plurality of lens groups, and at least one of the plurality of lens groups moves on an optical axis. Accordingly, it is possible to carry out the normal observation in a case in which an object point at a long distance is focused, and it is possible to carry out the magnified observation in a case in which an object point at a close distance is focused. In other words, an observation of a level equivalent to that of a microscopic observation as an extension of the magnified observation, and the magnified observation with even higher magnification are possible.

A basic arrangement of the objective optical system according to the present embodiment will be described below. In the basic arrangement, the objective optical system includes in order from an object side, a first lens group having a positive refractive power, a second lens group having a negative refractive power, and a third lens group having a positive refractive power. Focusing is carried out by moving the second lens group. The third lens group includes at least a positive lens and a cemented lens, and the cemented lens in the third lens group includes a positive lens and a negative lens. A first sub-lens group in the third lens group is positioned on the object side of a predetermined air space, and a second sub-lens group in the third lens group is positioned on an image side of the predetermined air space. The predetermined air space is the maximum air space among the air spaces in the third lens group.

In the basic arrangement, the objective optical system includes in order from the object side, the first lens group having a positive refractive power, the second lens group having a negative refractive power, and the third lens group having the positive refractive power. By making such arrangement, it is possible to suppress an aberration fluctuation at the time of focusing to be minimum, as well as to realize small-sizing of the overall optical system.

An object-point distance differs in the normal observation and the magnified observation. Moreover, from the time of the normal observation to the time of the magnified observation, the object-point distance varies continuously. Moreover, in an observation, even when the object-point distance varies, it is preferable that a sharp image be formed. For this, it is necessary to move at least one lens group.

In a case in which an objective optical system includes a plurality of lens groups, the lens group to be moved for focusing may be any lens group. Moreover, the number of the lens groups to be moved may be one or in plurality.

It is preferable that the number of the lens groups to be moved be small. When the number of the lens groups to be moved is let to be one, an effect that a drive mechanism can be simplified is exerted.

Moreover, even in a case of moving the plurality of lens groups, it is preferable that the number of the lens groups to be moved be small. For instance, in a case of moving the overall objective optical system, all the lens groups are to be moved. In this case, a weight of the lens groups to be moved becomes heavy. Consequently a load exerted to the drive mechanism becomes heavy, and moreover, the drive mechanism also becomes large in size. Therefore, it is not favorable to move all the lens groups.

Moreover, it is possible to keep the lens groups fixed, and to move an image pickup element instead of moving the lens groups. However, even in a case of moving the image pickup element, a drive mechanism becomes necessary. In a case in which the image pickup element is to be moved, a structure of the drive mechanism becomes complicated. Consequently, a weight of the drive mechanism becomes heavy. Moreover, a load exerted to the drive mechanism also becomes heavy, and the drive mechanism becomes large in size. Therefore, it is not favorable to move the image pickup element.

As described above, in the basic arrangement, focusing is carried out by moving the second lens group. Since the number of the lens groups to be moved is one, it is possible to simplify a focusing mechanism.

Figure 1B:
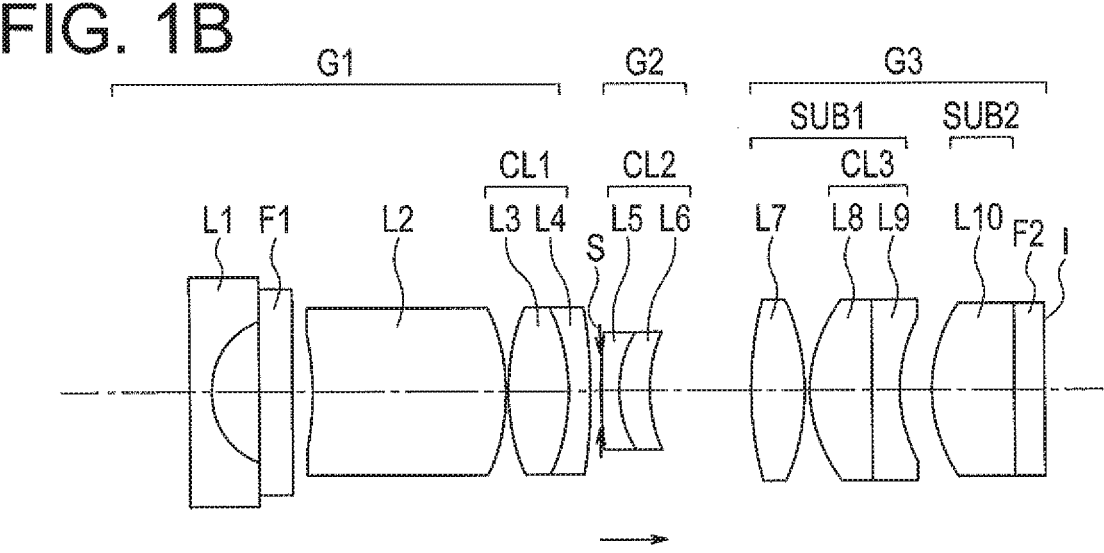

Specific arrangement examples of the basic arrangement will be described below. FIG. 1A and FIG. 1B are cross-sectional views showing a specific arrangement of the objective optical system according to the present embodiment, where, FIG. 1A is a cross-sectional view of an arrangement example 1 and FIG. 1B is a cross-sectional view of an arrangement example 2.

In the arrangement example 1, an objective optical system includes in order from an object side, a first lens group G1 having a positive refractive power, a second lens group G2 having a negative refractive power, and a third lens group G3 having a positive refractive power. An aperture stop S is disposed between the first lens group G1 and the second lens group G2.

The first lens group G1 includes in order from the object side, a first lens L1 having a negative refractive power, a second lens L2 having a positive refractive power, a third lens L3 having positive refractive power, and a fourth lens L4 having a negative refractive power. The third lens L3 and the fourth lens L4 are cemented and form a cemented lens CL1.

The second lens group G2 includes in order from the object side, a fifth lens L5 having a negative refractive power and a sixth lens L6 having a positive refractive power. The fifth lens L5 and the sixth lens L6 are cemented and form a cemented lens CL2. Since the refractive power of the second lens group G2 is a negative refractive power, the refractive power of the cemented lens CL2 is a negative refractive power.

In the arrangement example 1, focusing is carried out by moving the second lens group G2. FIG. 1A shows a state in which an object point at a long distance is focused. At a time of focusing to an object point at a close distance, the second lens group G2 moves toward an image side.

The third lens group G3 includes in order from the object side, a seventh lens L7 having a positive refractive power, an eighth lens L8 having a positive refractive power, and a ninth lens L9 having a negative refractive power. The eighth lens L8 and the ninth length L9 are cemented and form a cemented lens CL3.

The third lens group includes a first sub-lens group SUB1 and a second sub-lens group SUB2. The first sub-lens group SUB1 is positioned on the object side of a predetermined air space. The second sub-lens group SUB2 is positioned on the image side of the predetermined air space.

The predetermined air space is the maximum air space among air spaces in the third lens group G3. The predetermined air space is an air space between adjacent lenses.

In the arrangement example 1, the number of air spaces in the adjacent lenses is one. This air space is an air space between the seventh lens L7 and the eighth lens L8. Therefore, the air space between the seventh lens L7 and the eighth lens L8 is the predetermined air space. The first sub-lens group SUB1 includes the seventh lens L7. The second sub-lens group SUB2 includes the eighth lens L8 and the ninth lens L9.

A first plane parallel plate F1 is disposed between the first lens L1 and the second lens L2. The first plane parallel plate F1 may be disposed at an arbitrary position in the objective optical system. A second plane parallel plate F2 and a third plane parallel plate F3 are disposed on the image side of the third lens L9. The second plane parallel plate F2 and the third plane parallel plate F3 are cemented.

The second plane parallel plate F2 and the third plane parallel plate F3 are cover glasses of an image pickup element. An image pickup element (not shown in the diagram) is disposed on the image side of the third plane parallel plate F3. An image-side surface of the third plane parallel plate F3 is an image plane I. An image pickup surface of the image pickup element coincides with the image-side surface of the third plane parallel plate F3.

In the arrangement example 2, an objective optical system includes in order from an object side, a first lens group G1 having a positive refractive power, a second lens group G2 having a negative refractive power, and a third lens group G3 having a positive refractive power. An aperture stop S is disposed between the first lens group G1 and the second lens group G2.

The first lens group G1 includes in order from the object side, a first lens L1 having a negative refractive power, a second lens L2 having a positive refractive power, a third lens L3 having a positive refractive power, and a fourth lens L4 having a negative refractive power. The third lens L3 and the fourth lens L4 are cemented and form a cemented lens CL1.

The second lens group G2 includes in order from the object side, a fifth lens L5 having a negative refractive power and a sixth lens L6 having a positive refractive power. The fifth lens L5 and the sixth lens L6 are cemented and form a cemented lens CL2. Since the refractive power of the second lens group G2 is a negative refractive power, the refractive power of the cemented lens CL2 is a negative refractive power.

In the arrangement example 2, focusing is carried out by moving the second lens group G2. FIG. 1B shows a state in which an object point at a long distance is focused. At a time of focusing to an object point at a close distance, the second lens group G2 moves toward an image side.

The third lens group G3 includes in order from the object side, a seventh lens L7 having a positive refractive power, an eighth lens L8 having a positive refractive power, a ninth lens L9 having a negative refractive power, and a tenth lens L10 having a positive refractive power. The eighth lens L8 and the ninth lens L9 are cemented and form a cemented lens CL3.

The third lens group G3 includes a first sub-lens group SUB1 and a second sub-lens group SUB2. The first sub-lens group SUB1 is positioned on the object side of a predetermined air space. The second sub-lens group SUB2 is positioned on the image side of the predetermined air space.

In the arrangement example 2, the number of air spaces between adjacent lenses is two. A first air space is an air space between the seventh lens L7 and the eighth lens L8. A second air space is an air space between the ninth lens L9 and the tenth lens L10.

Out of the two air spaces, the second air space is larger than the first air space. Consequently, the air space between the ninth lens L9 and the tenth lens L10 becomes the predetermined air space. The first sub-lens group SUB1 includes the seventh lens L7, the eighth lens L8, and the ninth lens L9, and the second sub-lens group SUB2 includes the tenth lens L10.

A first plane parallel plate F1 is disposed between the first lens L1 and the second lens L2. The first plane parallel plate F1 may be disposed at an arbitrary position in the objective optical system. A second plane parallel plate F2 is disposed on the image side of the tenth lens L10. The second plane parallel plate F2 is cemented to the tenth lens L10.

The second plane parallel plate F2 is a cover glass of an image pickup element. An image pickup element (not shown in the diagram) is disposed on the image side of the second plane parallel plate F2. An image-side surface of the second plane parallel plate is an image plane I. The image pickup element is disposed such that an image pickup surface thereof coincides with the image-side surface of the second plane parallel plate F2.

An image-side surface of the tenth lens L10 may be let to be an image plane I. By making such arrangement, it is possible to stick the tenth lens L10 directly to the image pickup surface. In a case in which an image pickup unit includes an objective optical system and an image pickup element, by making such arrangement it is possible to shorten the image pickup unit.

In the arrangement example 2, the second sub-lens group SUB2 is cemented to the second plane parallel plate F2. Consequently, an image-side surface of the second sub-lens group SUB2 is restricted to be a flat surface.

Whereas, in the arrangement example 1, the second sub-lens group SUB2 and the second plane parallel plate F2 are disposed sandwiching an air space in between. In this case, it is possible to let an image-side surface of the second sub-lens group SUB2 to be a shape other than the flat shape. Consequently, in the arrangement example 1, it is possible set freely a magnitude of the refractive power of the second sub-lens group SUB2. As a result, in the arrangement example 1, it is possible to improve an aberration correction capacity than that in the arrangement example 2. In such manner, the arrangement example 1 is advantageous for making an image a high-quality image.

However, in the arrangement example 1, as compared to the arrangement example 2, the overall length of the optical system becomes long. In a case in which the overall length of the optical system is to be made short, it is desirable to make an arrangement of the objective optical system as the arrangement in the arrangement example 2.

In the arrangement example 1 and the arrangement example 2, the aperture stop S is disposed on the object side of the second lens group G2. By disposing the aperture stop S near the second lens group G2, it is possible to lower a height of a light ray passing through the second lens group G2. As a result, it is possible to make an outer diameter of the second lens group G2 small.

The second lens group G2 moves at the time of focusing. By the second lens group G2 being moved, even when an object point is positioned somewhere between a long distance to a close distance, it is possible to carry out focusing. It is possible to carry out the normal observation at a time of focusing to an object point at a long distance, and it is possible to carry out the magnified observation at a time of focusing to an object point at a close distance.

A moving mechanism becomes necessary for moving the second lens group G2 in an optical axial direction. As mentioned above, in the basic arrangement, since it is possible to make the second lens group G2 small-sized, it is possible to dispose easily the moving mechanism around the second lens group G2.

Moreover, since the number of the lens groups to be moved is one, it is possible to make light a weight of the lens group to be moved. Consequently, it is possible to reduce a load exerted to the moving mechanism. Furthermore, it is possible to make the moving mechanism simple.

An actuator is an example of the moving mechanism. An actuator is connected to a lens frame holding the second lens group G2, and accordingly, a drive force is imparted to the lens frame.

The third lens group G3 includes at least the positive lens and the cemented lens. Accordingly, it is possible to correct a spherical aberration and a chromatic aberration favorably. Each of the positive lens and the cemented lens may be in plurality.

In the first arrangement example and the second arrangement example, the first plane parallel plate F1 is disposed in the first lens group G1. The first plane parallel plate F1 is a filter for cutting off light of a specific wavelength, such as laser light of YAG (yttrium aluminum garnet) laser (light with a 106 nm wavelength), laser light of semiconductor laser (light with a 810 nm wavelength), or light of a wavelength in near-infrared region.

The objective optical system according to the present embodiment has the abovementioned basic arrangement, and the following conditional expression (1) is satisfied:

$$1.21 < fp/f < 2.42 \quad (1)$$

where, fp denotes a combined focal length from the first lens group up to the first sub-lens group, and f denotes a focal length of the overall objective optical system at the time of focusing to an object point at a long distance.

In the adjustment of the image position, the adjustment is carried out such that the ideal image plane coincides with the image position (image pickup surface). The objective optical system according to the present embodiment is an objective optical system compatible with a high-definition and small-sized image pickup element. In such objective optical system, the minimum diameter of a circle of confusion is extremely small, or, the adjustment sensitivity becomes high. For such reason, at the time of adjusting the image position, when the overall objective optical system is moved along an optical axis, the adjustment of the image position becomes difficult.

Therefore, in the objective optical system according to the present embodiment, at the time of adjusting the image position, some of the lenses (hereinafter, referred to as 'adjustment group') in the objective optical system are moved along the optical axis. By making such arrangement, the refractive power of the overall objective optical system is shared by the adjustment group and the remaining lenses (hereinafter, referred to as 'fixed group'). In other words, it is possible to make the refractive power of the adjustment group smaller than the refractive power of the overall objective optical system. As a result, it is possible to lower the adjustment sensitivity.

By making it possible to lower the adjustment sensitivity, it is possible to make an amount of movement of the adjustment group (hereinafter, referred to as 'adjustment quantity') large to some extent. Consequently, it is possible to move lenses accurately without complicating a mechanism which moves the lenses. In other words, it is possible to adjust the image position with a high accuracy. Moreover, when the adjustment sensitivity is low, an effect on various aberrations with respect to an occurrence of an error in the objective optical system after the adjustment is small, and it is possible to realize an objective optical system with a high imaging performance maintained as it had been.

It is preferable that the adjustment group include a lens positioned on the object side of the fixed group. For such reason, in the objective optical system according to the present embodiment, lens groups from the first lens group up to the first sub-lens group are let to be the adjustment group.

Conditional expression (1) is a conditional expression for letting the objective optical system to be an optical system most appropriate for the adjustment of the image position.

When a value falls below a lower limit value of conditional expression (1), there is almost no difference between the refractive power of the adjustment group and the refractive power of the overall objective optical system. In this case, since an effect of lowering the adjustment sensitivity is deteriorated, it becomes difficult to carry out the adjustment of the image position with a high accuracy. Consequently, in the objective optical system after the adjustment, it becomes difficult to realize a state in which an occurrence of various aberrations is suppressed.

Moreover, the significance of having the refractive power of the overall objective optical system having shared by the adjustment group and the fixed group almost ceases to exist. Therefore, it is not favorable that the value falls below the lower limit value of conditional expression (1).

When the value exceeds an upper limit value of conditional expression (1), the refractive power of the adjustment group becomes excessively small. In this case, although it is possible to lower the adjustment sensitivity, a focal length of the fixed group becomes relatively short. When the focal length of the fixed group becomes short, an amount of the spherical aberration occurring in the fixed group increases. Consequently, it becomes difficult to realize an objective optical system which is compatible with a high-definition image pickup element.

It is preferable that the following conditional expression (1') be satisfied instead of conditional expression (1).

$$1.3 < fp/f < 2.2 \quad (1')$$

By satisfying conditional expression (1'), the abovementioned effect becomes further larger. Consequently, it becomes possible to lower the adjustment sensitivity. By satisfying conditional expressions (1) or (1'), even with an optical system of any type of arrangement, it is possible to carry out the adjustment of the image position with a high accuracy. Consequently, it is possible to realize an objective optical system having a high imaging performance.

In the objective optical system of the present embodiment, it is preferable that the following conditional expression (2) be satisfied:

$$0.35 < tt/f < 0.6 \quad (2)$$

where, tt denotes the predetermined air space, and f denotes the focal length of the overall objective optical system at the time of focusing to an object point at a long distance.

As mentioned above, in the adjustment of the image position, the adjustment group is to be moved along the optical axis. The adjustment amount of the adjustment group is determined by a predetermined space. Therefore, conditional expression (2) signifies a conditional expression related to the adjustment amount.

When a value falls below a lower limit value of conditional expression (2), it becomes difficult to secure adequately the predetermined space. In this case, it is not possible to secure the adjustment amount adequately. Consequently, when a manufacturing error becomes large, it is not possible to carry out the adjustment of the image position.

When the value exceeds an upper limit value of conditional expression (2), it is possible to secure the adjustment amount adequately. However, since the adjustment amount becomes large, the overall length of the optical system becomes long. Moreover, it leads to a size of the frame member holding the lens becoming large. Therefore, it is not favorable that the value exceeds the upper limit value of conditional expression (2).

The predetermined air space can be regarded as a range in which the adjustment group is movable. In this case, the movable range becomes wider than a range (adjustment amount) necessary for the adjustment. When the value exceeds the upper limit value of conditional expression (2), since the predetermined space becomes wider than necessary, the overall length of the optical system becomes even longer.

In the objective optical system according to the present embodiment, it is preferable that the following conditional expression (1) be satisfied:

$$-15 < fG2/f < -5 \quad (3)$$

where, fG2 denotes a focal length of the second lens group, and f denotes the focal length of the overall objective optical system at the time of focusing to an object point at a long distance.

For forming a focused image even when the object distance varies, the objective optical system of the present embodiment has a focusing function. In focusing, the second lens group is moved in accordance with the variation in the object distance. A relationship between the object distance and the position in the optical axial direction of the second lens group at the time of focusing is determined at the time of designing. Therefore, in a case of carrying out focusing, the second lens group is to be moved according to the object distance, and the second lens group is to be brought to rest at a position at the time of designing.

At this time, it is preferable that the resting position of the second lens group and the position at the time of designing coincide. However, practically, there is an error between the resting position of the second lens group and the position at the time of designing. When a proportion of an amount of focal shift with respect to an amount of error (hereinafter, referred to as 'error sensitivity at the time of focusing') is high, even when the amount of error is small, a focused image is not formed at the image position.

By satisfying conditional expression (3), it is possible to lower the error sensitivity at the time of focusing, and moreover, it is also possible to suppress an aberration fluctuation at the time of focusing.

When a value falls below a lower limit value of conditional expression (3), a fluctuation in a curvature of field accompanying the movement of the second lens group becomes large. In this case, there is a remarkable difference between the image position at the time of normal observation and the image position at the time of close observation. Therefore, it is not favorable that the value falls below a lower limit value.

When the value exceeds an upper limit value of conditional expression (3), the refractive power of the second lens group becomes large. In this case, the error sensitivity at the time of focusing becomes high.

Moreover, decentering such as tilt and shift occurs sometimes in the second lens group. In a case in which the error sensitivity at the time of focusing is high, even when an amount of decentering of the lens group is minimal, deterioration of imaging performance becomes remarkable. For such reason, it is not favorable that the value exceeds the upper limit value of conditional expression (3).

In the objective optical system according to the present embodiment, it is possible to carry out the normal observation and the magnified observation. Therefore, a focusing range on the object side is wide. In such objective optical system, it is necessary to suppress further a fluctuation in the image-plane position when switched over from the normal observation to the magnified observation.

For suppressing the fluctuation in the image-plane position, the fluctuation in the curvature of field, when switched from the normal observation to the magnified observation, is to be made even smaller. For such reason, it is preferable that the following conditional expression (3') be satisfied instead of conditional expression (3).

$$-11 < fG2/f < -5 \quad (3')$$

By satisfying conditional expression (3'), it is possible to reduce further the fluctuation in the image-plane position at the time of focusing.

In the objective optical system according to the present embodiment, it is preferable that the following conditional expression (4) be satisfied:

$$0.7 < fG3SUB1/fG3SUB2 < 1.4 \quad (4)$$

where, fG3SUB1 denotes a focal length of the first sub-lens group, and fG3SUB2 denotes a focal length of the second sub-lens group.

In the adjustment of the image position, the second sub-lens group is fixed with respect to the image position. Moreover, lens groups from the first lens group up to the first sub-lens group are to be moved. Consequently, in the adjustment of the image position, a distance between the first sub-lens group and the second sub-lens group varies. In a case in which the aberration fluctuation when this distance was varied is large, the image performance is deteriorated at the time of adjusting the image position. It is possible to suppress to minimum the aberration fluctuation that occurs at the time of adjusting the image position, particularly the fluctuation in the curvature of field, by making appropriate the refractive power of the first sub-lens group and the second sub-lens group.

Conditional expression (4) is a conditional expression of a ratio of the refractive power of the first sub-lens group and the refractive power of the second sub-lens group. By satisfying conditional expression (4), it is possible to make appropriate both the refractive power of the first sub-lens group and the refractive power of the second sub-lens group. Consequently, at the time of adjusting the image position, it is possible to make small the fluctuation in aberration, and particularly the fluctuation in the curvature of field.

When a value falls below a lower limit value of conditional expression (4), the curvature of field becomes excessively over. Moreover, when the value exceeds an upper limit value of conditional expression (4), the curvature of field becomes excessively inadequate. In any of the cases, since an amount of the curvature of field that occurs is large, at the time of adjusting the image position, the fluctuation in the curvature of field becomes large.

In the objective optical system according to the present embodiment, it is preferable that the following conditional expression (5) be satisfied:

$$-6 < fG2/fG1 < -2 \quad (5)$$

where, fG2 denotes the focal length of the second lens group, and fG1 denotes a focal length of the first lens group.

Conditional expression (5) is a conditional expression for making the refractive power of the second lens group a refractive power of an appropriate magnitude. By satisfying conditional expression (5), it is possible to make the refractive power of the second lens group of an appropriate magnitude. As a result, it is possible to suppress the fluctuation in the image-plane position at the time of focusing, and moreover, to make the optical system small-sized.

When a value falls below a lower limit value of conditional expression (5), the refractive power of the second lens group becomes small. In this case, an amount of movement of the second lens group at the time of focusing becomes excessively large. Consequently, the optical system becomes large in size.

When the value exceeds an upper limit value of conditional expression (5), the fluctuation in the curvature of field accompanying the focusing becomes large. In this case, there is a remarkable difference between the image position at the time of normal observation and the image position at the time of magnified observation. Therefore, it is not favorable that the value exceeds the upper limit value of conditional expression (5).

In the objective optical system according to the present embodiment, it is preferable that the following conditional expression (6) be satisfied:

$$-7.6 < fG2/fG3 < -2.4 \quad (6)$$

where, fG2 denotes the focal length of the second lens group, and fG3 denotes a focal length of the third lens group.

Conditional expression (6) is a conditional expression related to correction of the curvature of field. By satisfying conditional expression (6), it is possible to correct the curvature of field favorably.

When a value falls below a lower limit value of conditional expression (6), the curvature of field becomes excessively over. When the value exceeds an upper limit value of conditional expression (6), the curvature of field becomes excessively inadequate. In any of the cases, since the image plane is inclined, it is not possible to focus at one of a central portion and a peripheral portion of an image.

In the objective optical system according to the present embodiment, it is preferable that the following conditional expression (7) be satisfied:

$$1.0 < fG3/fG1 < 2.0 \quad (7)$$

where, fG3 denotes the focal length of the third lens group, and fG1 denotes the focal length of the first lens group.

Conditional expression (7) is a conditional expression related to correction of a chromatic aberration of magnification. By satisfying conditional expression (7), it is possible to correct the chromatic aberration of magnification favorably.

When a value falls below a lower limit value of conditional expression (7), a difference between the chromatic aberration of magnification for a C-line and the chromatic aberration of magnification for an F-line is corrected excessively. Moreover, for a longitudinal chromatic aberration, a balance of an aberration amount for each wavelength is disrupted. Therefore, it is not favorable that the value falls below the lower limit value of conditional expression (7).

When the value exceeds an upper limit value of conditional expression (7), correction of the chromatic aberration of magnification becomes inadequate. Therefore, it is not favorable that the value exceeds the upper limit value of conditional expression (7).

In a case of not satisfying conditional expression (7), chromatic blurring occurs in a peripheral portion of an image. Consequently, it leads to a degradation of contrast in the peripheral portion of the image.

In the objective optical system according to the present embodiment, it is preferable that the following conditional expression (8) be satisfied:

$$1.4 < (t12+t23)/f < 3.2 \quad (8)$$

where, t12 denotes a distance between the first lens group and the second lens group at the time of focusing to an object point at a long distance, t23 denotes a distance between the second lens group and the third lens group at the time of focusing to an object point at a long distance, and f denotes the focal length of the overall objective optical system at the time of focusing to an object point at a long distance.

Conditional expression (8) is a conditional expression related to an amount of movement of lens groups at the time of focusing.

When a value falls below a lower limit value of conditional expression (8), a distance between the first lens group and the third lens group becomes short. Consequently, it becomes difficult to secure a space necessary for movement of the second lens group.

In the magnified observation, an object distance is approximately 2 mm. In objective optical system of an endoscope, it is necessary to be able to focus up to an object positioned at such a close distance. Therefore, in a case in which it is not possible to secure the space necessary for the movement of the second lens group, an object positioned at a close distance cannot be focused. As a result, the magnified observation with a high magnification becomes difficult.

When it is not possible to secure adequately the space necessary for the movement of the second lens group, the second lens group is to be moved in a narrow space. Consequently, the refractive power of the second lens group is to be made large.

As mentioned above, the resting position of the second lens group at the time of focusing is determined at the time of designing. When the refractive power of the second lens group is large, even in a case in which the difference between the resting position of the second lens group and the position at the time of designing is large, a focused image is not formed at the image position.

Furthermore, even in a case in which the amount of movement of the second lens group is made small in order to be accommodated in this space, the error sensitivity at the time of focusing becomes high. Moreover, a trouble due to a manufacturing error, such as a shift in the image-plane position with respect to a shift in the position of the second lens group becoming large, is susceptible to occur.

When an upper limit value of conditional expression (8) is exceeded, the distance between the first lens group and the third lens group becomes excessively long. In this case, although it is possible to secure the space necessary for the movement of the second lens group, the optical system becomes large in size.

It is more preferable that the following conditional expression (8') be satisfied instead of conditional expression (8).

$$1.8 < (t12+t23)/f < 2.9 \quad (8')$$

By satisfying conditional expression (8'), it is possible to realize securing the minimum space necessary for the movement of the second lens group and adequate small-sizing of the optical system.

In the objective optical system according to the present embodiment, it is preferable that the first lens group include a first lens, and the following conditional expression (9) be satisfied.

$$-0.8 < fL1/fG1 < -0.5 \quad (9)$$

where, fL1 denotes a focal length of the first lens, and
fG1 denotes a focal length of the first lens group.

Conditional expression (9) is a conditional expression related to lowering error sensitivity for the angle of view. An error in an air space between the first lens and the second lens (hereinafter, referred to as 'space L12') contributes largely to a fluctuation in the angle of view as compared to an error in a distance between other lenses. By setting the focal length of the first lens to satisfy conditional expression (9), it is possible to realize an objective optical system which is strong with respect to the manufacturing error.

When a value falls below a lower limit value of conditional expression (9), the refractive power of the first lens becomes small. In this case, the error sensitivity for the angle of view is lowered. However, in a case in which an attempt is made to adjust the angle of view to an appropriate angle of view by varying the space L12, the adjustment amount, or in other words, a value of the space L12 becomes excessively large. Consequently, the overall length of the optical system becomes long. Therefore, it is not favorable that the value falls below the lower limit value of conditional expression (9).

When the value exceeds an upper limit value of conditional expression (9), the refractive power of the first lens becomes excessively large. In this case, the error sensitivity with respect to the angle of view becomes high. When an attempt is made to adjust the angle of view to an appropriate angle of view by varying the space L12, the adjustment becomes difficult.

Moreover, the second lens group is moved at the time of focusing. When there is an error in the resting position of the second lens group, even with the adjustment of the angle of view carried out at the time of manufacturing, the angle of view varies largely at the time of using. In such manner, in a case in which the error has occurred after the adjustment, the variation in the angle of view due to the error also becomes large. Therefore, it is not favorable that the value exceeds the upper limit value of conditional expression (9).

In the objective optical system according to the present embodiment, it is preferable that the following conditional expression (10) be satisfied:

$$1.8 < rG3SUB2F/f < 5.2 \quad (10)$$

where, rG3SUB2F denotes a radius of curvature of a lens surface positioned nearest to object of the second sub-lens group, and f denotes the focal length of the overall objective optical system at the time of focusing to an object point at a long distance.

Conditional expression (10) is an expression for making appropriate an angle of a principal light ray incident on the image plane (hereinafter, referred to as 'angle of incidence'). This angle is an angle made by the principal light ray and the optical axis. In a case of capturing an image by an image pickup element, an image pickup surface of the image pickup element substitutes the image plane. Therefore, in this case, the angle of the principal light ray incident on the image pickup surface is also referred to as the angle of incidence.

In an image pickup element, the larger the angle of incidence, smaller is an amount of light detected by a pixel. Even when the angle of incidence is the same, the smaller an area of the pixel, smaller is the amount of light detected. In a small-sized and high-definition image pickup element, the area of a pixel is small. Therefore, in a small-sized and high-definition image pickup element, it is necessary to keep the angle of incidence small to a certain level.

In a lens disposed nearest to the image plane, the principal light ray is refracted to be closer to the optical axis. When a value falls below a lower limit value of conditional expression (10), the principal light ray is refracted substantially. In this case, the objective optical system becomes a telecentric optical system. In a telecentric optical system, the angle of incidence becomes small. Therefore, even when a small-sized and high-definition image pickup element is used, it is possible to acquire a bright image.

However, since a light-ray height becomes high, the lens becomes large in diameter. Moreover, an amount of the spherical aberration that occurs at a surface of incidence of a lens disposed nearest to the image plane becomes large.

When the value exceeds an upper limit value of conditional expression (10), the angle of incidence becomes large. In this case, for a pixel positioned on a periphery of the image pickup surface, an amount of light detected becomes small. As a result, peripheral darkening occurs in an image captured.

When the value exceeds the upper limit value of conditional expression (10), conditional expression (1) cannot be satisfied. Consequently, the effect of lowering the adjustment sensitivity is deteriorated.

It is more preferable that the following conditional expression (10') be satisfied instead of conditional expression (10).

$$2.3 < rG3SUB2F/f < 4.9 \quad (10')$$

By satisfying conditional expression (10'), it is possible to make the optical system further small-sized, and to further lower the adjustment sensitivity.

In the objective optical system according to the present embodiment, it is preferable that the third lens group include in order from the object side, a positive lens and a cemented lens.

When such arrangement is made, the cemented lens is positioned on the image side. Consequently, it is possible to make small the longitudinal chromatic aberration and the chromatic aberration of magnification that occur.

In this case, the first sub-lens group includes the positive lens and the second sub-lens group includes the cemented lens.

In the objective optical system according to the present embodiment, it is preferable that the third lens group further include another cemented lens, and the another cemented lens includes a positive lens and a negative lens.

By making such arrangement, it is possible to correct a chromatic aberration favorably.

In the objective optical system according to the present embodiment, it is preferable that the third lens group include in order from the object side, a positive lens, a cemented lens, and another cemented lens.

When such arrangement is made, the two cemented lenses are positioned nearest to image. Consequently, it is possible to make further smaller the longitudinal chromatic aberration and the chromatic aberration of magnification that occur.

In this case, the first sub-lens group includes the positive lens and the second sub-lens group includes the cemented lens and the another cemented lens.

Or, it is preferable that the first sub-lens group includes the positive lens and the cemented lens, and the second sub-lens group includes the another cemented lens.

In the objective optical system according to the present embodiment, it is preferable that the third lens group include further, another positive lens.

By making such arrangement, it is possible to correct the spherical aberration even more favorably.

In the objective optical system according to the present embodiment, it is preferable that the third lens group include in order from the object side, a positive lens, another positive lens, and a cemented lens.

When such arrangement is made, the cemented lens is positioned nearest to image. Consequently, it is possible to make small the longitudinal chromatic aberration and the chromatic aberration of magnification that occur.

Moreover, by the another positive lens and the cemented lens, it becomes possible to suppress the spherical aberration to be small. Consequently, it is possible to reduce an aberration fluctuation at the time of adjustment of the image position.

In this case, it is preferable that the first sub-lens group SUB1 include the positive lens, and the second sub-lens group SUB2 include the positive lens and the cemented lens.

In the objective optical system according to the present embodiment, it is preferable that the third lens group include in order from the object side, a positive lens, a cemented lens, and another positive lens.

When such arrangement is made, the cemented lens is positioned on the image side. Consequently, it is possible to make small the longitudinal chromatic aberration and the chromatic aberration of magnification that occur.

In this case, it is preferable that the first sub-lens group include the positive lens and the cemented lens, and the second sub-lens group include the cemented lens.

In the objective optical system according to the present embodiment, it is preferable that the following conditional expression (11) be satisfied:

$$4.0 < fG3SUB2F/f < 6.5 \qquad (11)$$

where, fG3SUB2F denotes a focal length of a predetermined lens surface, and f denotes the focal length of the overall objective optical system at the time of focusing to an object point at a long distance, and the predetermined lens surface is a lens surface positioned nearest to object of the second sub-lens group.

Conditional expression (11) is a conditional expression related to lowering the adjustment sensitivity.

When a proportion of an amount of degradation of a lens performance at periphery with respect to decentering of a single component or an optical system at the time of manufacturing (hereinafter, referred to as 'error sensitivity for lens performance at periphery') is high, an imaging performance at the periphery of an image is degraded.

When a value falls below a lower limit value of conditional expression (11), the error sensitivity for the lens performance at periphery becomes high. Moreover, an effect on an angle of deviation becomes large. Therefore, it is not favorable that the value falls below the lower limit value of conditional expression (11).

In an objective optical system as in the arrangement example 2, it is possible to lower the adjustment sensitivity. However, since there is only one lens surface which determines the refractive power of a lens, a radius of curvature of the lens surface becomes small. As a result, the error sensitivity for the lens performance at periphery becomes high. Moreover, an effect on the angle of deviation is also remarkable.

When the value exceeds an upper limit value of conditional expression (11), since the refractive power of the second sub-lens group in the optical system becomes small, the refractive power of a moving unit becomes relatively large. In this case, the adjustment sensitivity becomes high. Consequently, the adjustment of the image position becomes difficult.

It is more preferable that the one of the following conditional expression (11') or (11") be satisfied instead of conditional expression (11).

$$4.5 < fG3SUB2F/f < 6.5 \qquad (11')$$

$$4.0 < fG3SUB2F/f < 5.5 \qquad (11'')$$

By satisfying conditional expressions (11') or (11"), it is possible to further lower the adjustment sensitivity. As a result, it is possible to reduce the manufacturing cost.

In the objective optical system according to the present embodiment, it is preferable that the lens positioned nearest to image in the third lens group be a planoconvex lens, and an object-side surface of the planoconvex lens be a surface which is convex toward the object side.

By making such arrangement, it is possible to refract a light ray incident on the image plane to be closer to the optical axis.

Since an image-side surface of the planoconvex lens is a flat surface, it is possible to stick to the image pickup surface or to stick to a cover glass of the image pickup element.

It is preferable that the objective optical system according to the present embodiment includes a predetermined cemented lens, and the predetermined cemented lens is disposed to be adjacent to the aperture stop, on the object side of the aperture stop.

In order to be compatible with a high-definition image pickup element, correction of the longitudinal chromatic aberration becomes significant. By making the abovementioned arrangement, the cemented lens is disposed immediately before the aperture stop. Accordingly, it is possible to correct the longitudinal chromatic aberration adequately. As a result, it is compatible with a high-definition image pickup element.

In the objective optical system according to the present embodiment, it is preferable that a predetermined cemented lens be disposed nearest to image in the first lens group, and include a biconvex lens and a negative meniscus lens having a convex surface directed toward the image side.

In the objective optical system according to the present embodiment, it is preferable that the following conditional expression (12) be satisfied:

$$3.0 < fG1CL/rG1CL < -0.7 \qquad (12)$$

where, fG1CL denotes a focal length of the predetermined cemented lens, and rG1CL denotes a radius of curvature of a cemented surface of the predetermined cemented lens.

Conditional expression (12) is a conditional expression related to correction of the longitudinal chromatic aberration.

When a value falls below a lower limit value of conditional expression (12), correction of the longitudinal chromatic aberration become excessive, and moreover, the spherical aberration becomes inadequate and the chromatic aberration of magnification also becomes substantial. Therefore, it is not favorable that the value falls below the lower limit value of conditional expression (12).

When the value exceeds an upper limit value of conditional expression (12), correction of the longitudinal chromatic aberration becomes inadequate. As a result, a contrast of an image is degraded. Therefore, it is not favorable that the value exceeds the upper limit value of conditional expression (12).

In the objective optical system of the present embodiment, it is preferable that the first lens group include in order from the object side, at least a planoconcave lens having a concave surface directed toward the image side, a positive meniscus lens having a convex surface directed toward the image side, a biconvex lens, and a negative meniscus lens having a convex surface directed toward the image side.

By making such arrangement, it is possible to correct the longitudinal chromatic aberration and the chromatic aberration of magnification in a balanced manner. Moreover, it is also possible to correct the curvature of field favorably.

In the objective optical system according to the present embodiment, it is preferable that the biconvex lens and the negative meniscus lens having the convex surface directed toward the image side be cemented.

When a shape of the positive lens in the cemented lens is a biconvex shape, it is possible to correct the spherical aberration favorably.

In the objective optical system according to the present embodiment, it is preferable that the first lens group include in order from the object side, at least a planoconcave lens having a concave surface directed toward the image side, a positive meniscus lens having a convex surface directed toward the image side, a negative meniscus lens having a convex surface directed toward the image side, a biconvex positive lens, and a negative meniscus lens having a convex surface directed toward the image side.

In the objective optical system according to the present embodiment, it is preferable that the positive meniscus lens having the convex surface directed toward the image side, and a negative meniscus lens having the convex surface directed toward the image side bee cemented.

By making such arrangement, it is possible to correct the longitudinal chromatic aberration more adequately.

It is also possible to use the objective optical system according to the present embodiment in an optical instrument other than endoscope.

For instance, it is possible to use the objective optical system according to the present embodiment for an image pickup optical system of a digital camera. In photographing with a digital camera, sometimes, a macrophotography beyond equal magnification is to be carried out. In such case, sometimes, an amount of drawing out of a lens becomes large, and a macro converter lens is to be mounted in many cases. However, by using the objective optical system of the present embodiment as an image pickup optical system, it is possible to carry out macrophotography with a high magnification higher than ever before, without installing the macro converter lens.

Moreover, generally, with a macro lens, focusing is carried out by drawing the first lens group toward the object side, and floating a plurality of lens groups. On the other hand, when the objective optical system of the present embodiment is used, it is possible to carry out macrophotography by an inner focusing. Therefore, it is advantageous in a case of photographing after determining a working distance.

Furthermore, it is possible to use the objective optical system according to the present embodiment in portable equipment such as an image pickup optical system of a camera of portable telephones. By making such arrangement, the macrophotography can be readily enjoyable.

Example 1

Figure 2A:
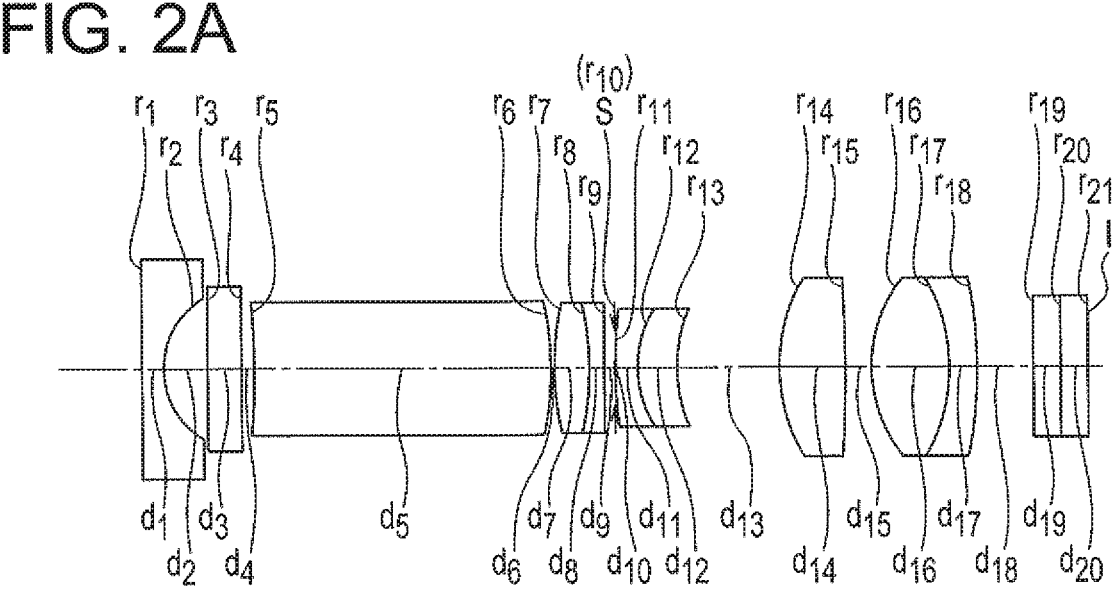
FIG. 2A and FIG. 2B are cross-sectional views of an objective optical system of an example 1.
Figure 2B:
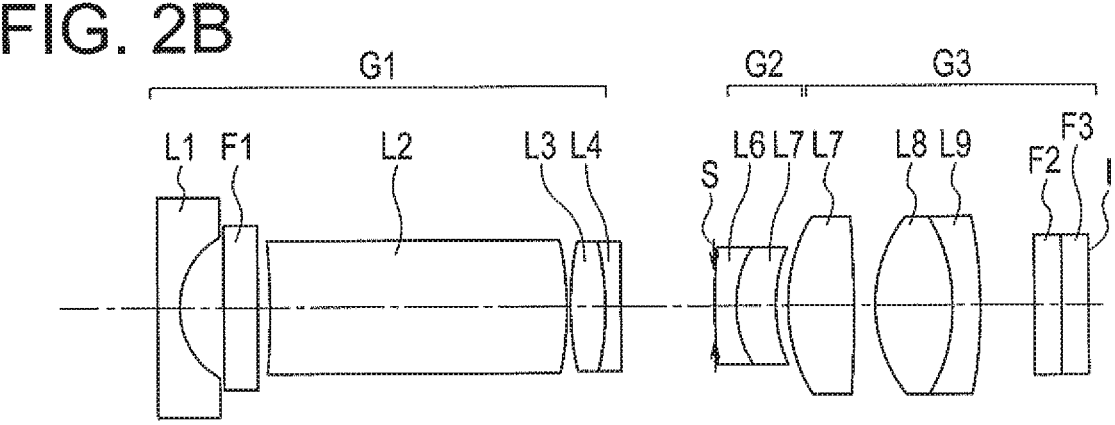

An objective optical system according to an example 1 will be described below. FIG. 2A and FIG. 2B are lens cross-sectional views of the objective optical system according to the example 1, where, FIG. 2A is a cross-sectional view in a normal observation state, and FIG. 2B is a cross-sectional view in a magnified observation state.

The objective optical system of the example 1, as shown in FIG. 2A and FIG. 2B, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a biconvex positive lens L3, and a planoconcave negative lens L4 of which an image side is a flat surface. Here, the biconvex positive lens L3 and the planoconcave negative lens L4 are cemented to form a cemented lens.

The second lens group G2 includes a negative meniscus lens L5 having a convex surface directed toward the object side and a positive meniscus lens L6 having a convex surface directed toward the object side. Here, the negative meniscus lens L5 and the positive meniscus lens L6 are cemented to form a cemented lens.

An aperture stop S is disposed between the first lens group G1 and the second lens group G2. More specifically, the aperture stop S is disposed nearest to object in the second lens group G2.

The third lens group G3 includes a biconvex positive lens L7, a biconvex positive lens L8, and a negative meniscus lens L9 having a convex surface directed toward the image side. Here, the biconvex positive lens L8 and the negative meniscus lens L9 are cemented to form a cemented lens.

A first sub-lens group SUB1 includes the biconvex positive lens L7. A second sub-lens group SUB2 includes the biconvex positive lens L8 and the negative meniscus lens L9.

A plane parallel plate F1 is disposed on the image side of the planoconcave negative lens L1. A plane parallel plate F2 and a plane parallel plate F3 are disposed on the image side of the third lens group G3.

At a time of focusing, the second lens group G2 and the aperture stop S move integrally. At the time of focusing to an object point at a close distance from a state of being focused to an object point at a long distance, the second lens group G2 and the aperture stop S move toward the image side.

The objective optical system of the example 1 has the abovementioned basic arrangement, and also satisfies each of conditional expressions (1) to (12).

FIG. 3A, FIG. 3B, FIG. 3C, and FIG. 3D are aberration diagrams of a spherical aberration (SA), an astigmatism (AS), a distortion (DT), and a chromatic aberration of magnification (CC) respectively, in a normal observation state of the example 1. FIG. 3E, FIG. 3F, FIG. 3G, and FIG. 3H are aberration diagrams of a spherical aberration (SA), an astigmatism (AS), a distortion (DT), and a chromatic aberration of magnification (CC) respectively, in a magnified observation state of the example 1.

In each aberration diagram, a horizontal axis indicates an aberration amount. For the spherical aberration, the astigmatism, and the chromatic aberration of magnification, the unit of aberration amount is mm. Moreover, for the distortion, the unit of aberration amount is %. Furthermore, ω denotes a half angle of view and the unit thereof is ° (degrees), and FNO denotes an F-number. Moreover, the unit of a wavelength of an aberration curve is nm. These units are same for other examples as well.

Figure 4A:
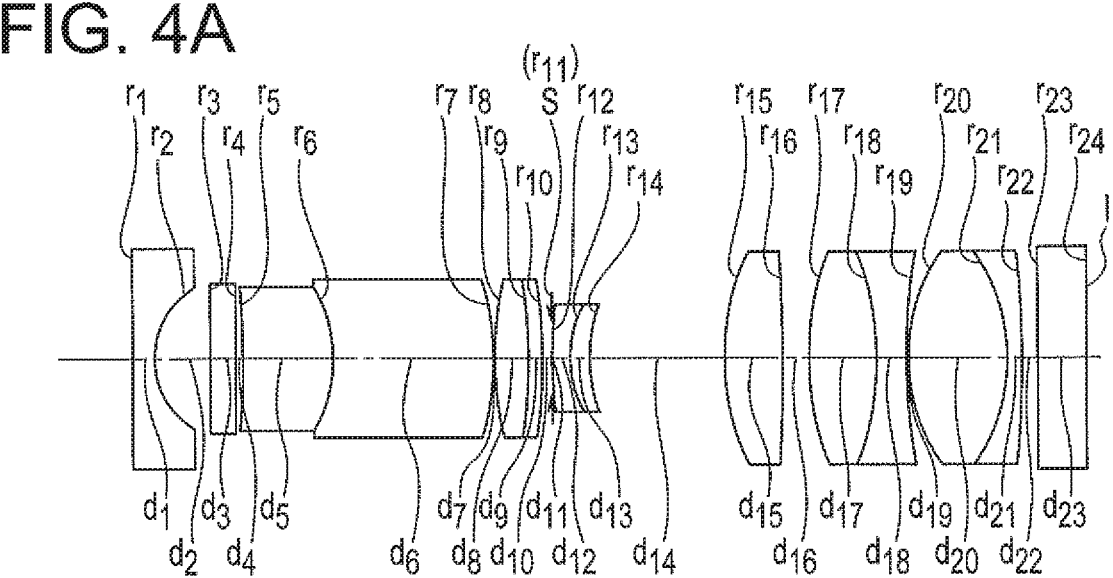
FIG. 4A and FIG. 4B are cross-sectional views of an objective optical system of an example 2.
Figure 4B:
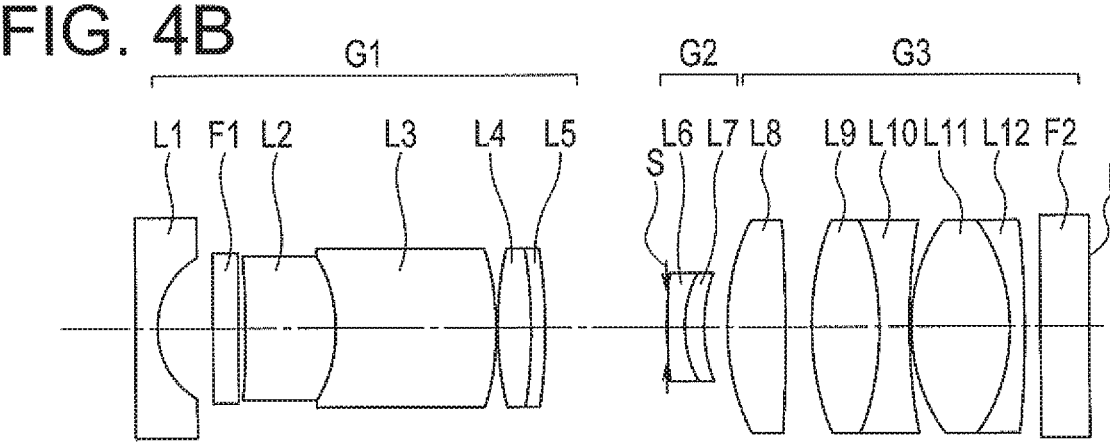

An objective optical system according to an example 2 will be described below. FIG. 4A and FIG. 4B are lens cross-sectional views of the objective optical system according to the example 2, where, FIG. 4A is a cross-sectional view in a normal observation state, and FIG. 4B is a cross-sectional view in a magnified observation state.

The objective optical system of the example 2, as shown in FIG. 4A and FIG. 4B, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a biconvex positive lens L4, and a negative meniscus lens L5 having a convex surface directed toward the image side. Here, the positive meniscus lens L2 and the negative meniscus lens L3 are cemented to form a cemented lens. The biconvex positive lens L4 and the negative meniscus lens L5 are cemented to form a cemented lens.

The second lens group G2 includes a negative meniscus lens L6 having a convex surface directed toward the object side and a positive meniscus lens L7 having a convex surface directed toward the object side. Here, the negative meniscus lens L6 and the positive meniscus lens L7 are cemented to forma cemented lens.

An aperture stop S is disposed between the first lens group G1 and the second lens group G2. More specifically, the aperture stop S is disposed nearest to object in the second lens group.

The third lens group G3 includes a positive meniscus lens L8 having a convex surface directed toward the object side, a biconvex positive lens L9, a biconcave negative lens L10, a biconvex positive lens L11, and a negative meniscus lens L11 having a convex surface directed toward the image side. Here, the biconvex positive lens L9 and the biconcave negative lens L10 are cemented to form a cemented lens. The biconvex positive lens L11 and the negative meniscus lens L12 are cemented to form a cemented lens.

A first sub-lens group SUB1 includes the positive meniscus lens L8. A second sub-lens group SUB2 includes the biconvex positive lens L9, the biconcave negative lens L10, the biconvex positive lens L11, and the negative meniscus lens L12.

A plane parallel plate F1 is disposed on the image side of the planoconcave negative lens L1. A plane parallel plate F2 is disposed on the image side of the third lens group G3.

At a time of focusing, the second lens group G2 and the aperture stop S move integrally. At the time of focusing to an object point at a close distance from a state of being focused to an object point at a long distance, the second lens group G2 and the aperture stop S move toward the image side.

The objective optical system of the example 2 has the abovementioned basic arrangement, and also satisfies each of conditional expressions (1) to (12).

FIG. 5A, FIG. 5B, FIG. 5C, and FIG. 5D are aberration diagrams of a spherical aberration (SA), an astigmatism (AS), a distortion (DT), and a chromatic aberration of magnification (CC) respectively, in a normal observation state of the example 2. FIG. 5E, FIG. 5F, FIG. 5G, and FIG. 5H are aberration diagrams of a spherical aberration (SA), an astigmatism (AS), a distortion (DT), and a chromatic aberration of magnification (CC) respectively, in a magnified observation state of the example 2.

Figure 6A:
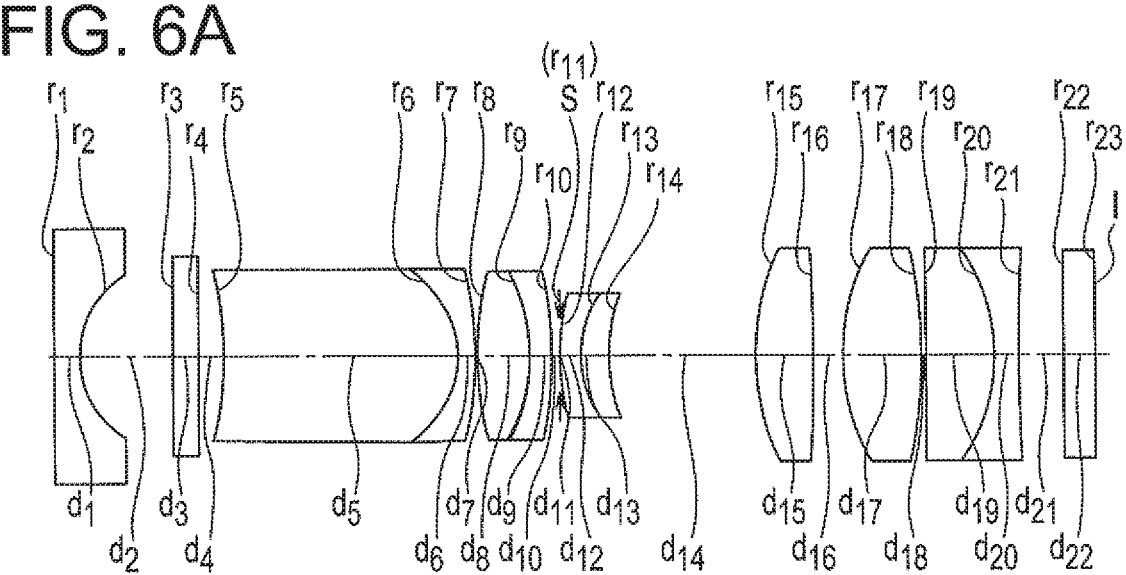
FIG. 6A and FIG. 6B are cross-sectional views of an objective optical system of an example 3.
Figure 6B:
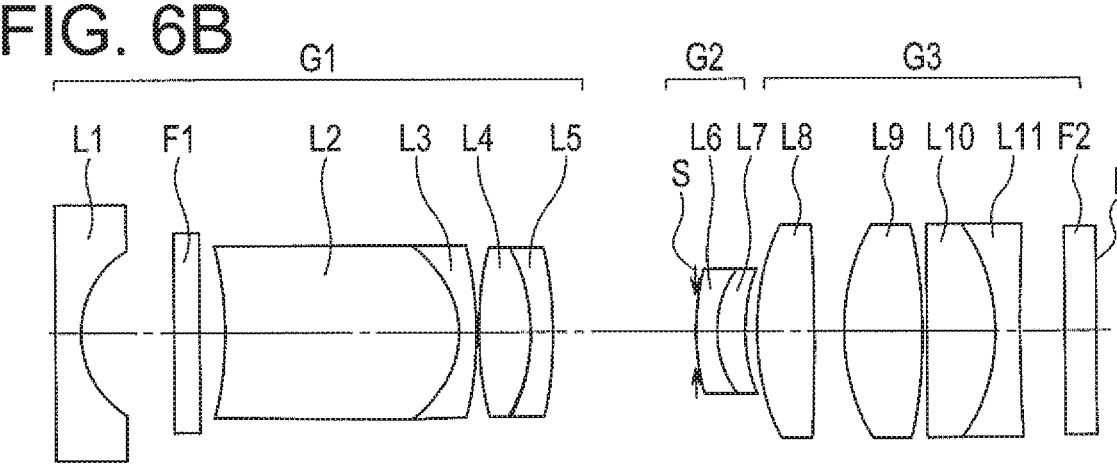

An objective optical system according to an example 3 will be described below. FIG. 6A and FIG. 6B are lens cross-sectional views of the objective optical system according to the example 3, where, FIG. 6A is a cross-sectional view in a normal observation state, and FIG. 6B is a cross-sectional view in a magnified observation state.

The objective optical system of the example 3, as shown in FIG. 6A and FIG. 6B, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a biconvex positive lens L4, and a negative meniscus lens L5 having a convex surface directed toward the image side. Here, the positive meniscus lens L2 and the negative meniscus lens L3 are cemented to form a cemented lens. The biconvex positive lens L4 and the negative meniscus lens L5 are cemented to form a cemented lens.

The second lens group G2 includes a negative meniscus lens L6 having a convex surface directed toward the object side and a positive meniscus lens L7 having a convex surface directed toward the object side. Here, the negative meniscus lens L6 and the positive meniscus lens L7 are cemented to form a cemented lens.

An aperture stop S is disposed between the first lens group G1 and the second lens group G2. More specifically, the aperture stop S is disposed nearest to object in the second lens group G2.

The third lens group G3 includes a biconvex positive lens L8, a biconvex positive lens L9, a biconvex positive lens L10, and a biconcave negative lens L11. Here, the biconvex positive lens L10 and the biconcave negative lens L11 are cemented to form a cemented lens.

A first sub-lens group SUB1 includes the positive meniscus lens L8. A second sub-lens group SUB2 includes the biconvex positive lens L9, the biconvex positive lens L10, and the biconcave negative lens L11.

A plane parallel plate F1 is disposed on the image side of the planoconcave negative lens L1. A plane parallel plate F2 is disposed on the image side of the third lens group G3.

At a time of focusing, the second lens group G2 and the aperture stop S moves integrally. At the time of focusing to an object point at a close distance from a state of being focused to an object point at a long distance, the second lens group G2 and the aperture stop S move toward the image side.

The objective optical system of the example 3 has the abovementioned basic arrangement, and also satisfies each of conditional expressions (1) to (12).

FIG. 7A, FIG. 7B, FIG. 7C, and FIG. 7D are aberration diagrams of a spherical aberration (SA), an astigmatism (AS), a distortion (DT), and a chromatic aberration of magnification (CC) respectively, in a normal observation state of the example 3. FIG. 7E, FIG. 7F, FIG. 7G, and FIG. 7H are aberration diagrams of a spherical aberration (SA), an astigmatism (AS), a distortion (DT), and a chromatic aberration of magnification (CC) respectively, in a magnified observation state of the example 3.

Example 4

Figure 8A:
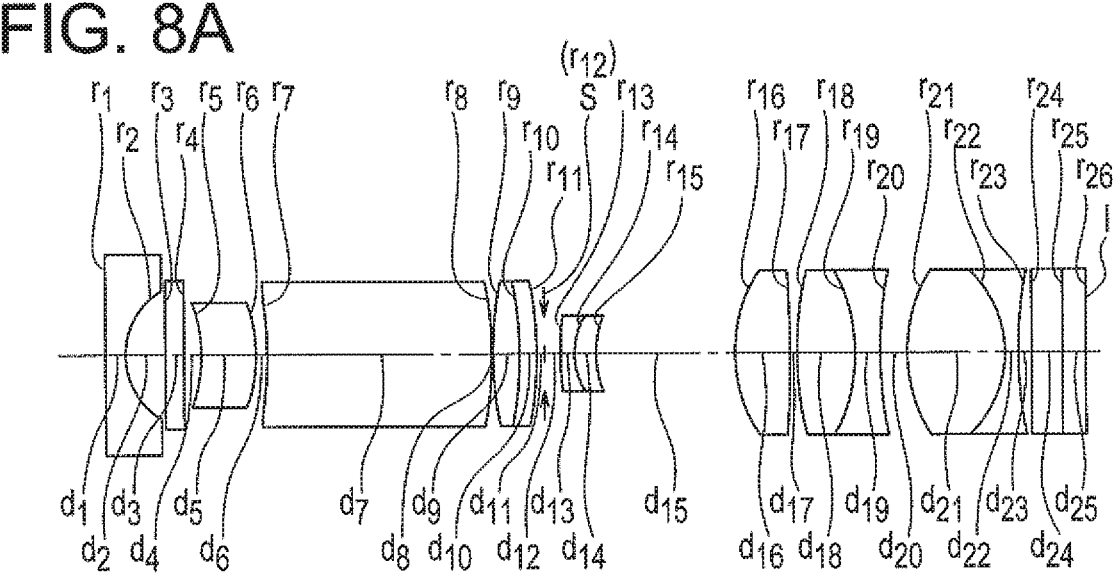
FIG. 8A and FIG. 8B are cross-sectional views of an objective optical system of an example 4.
Figure 8B:
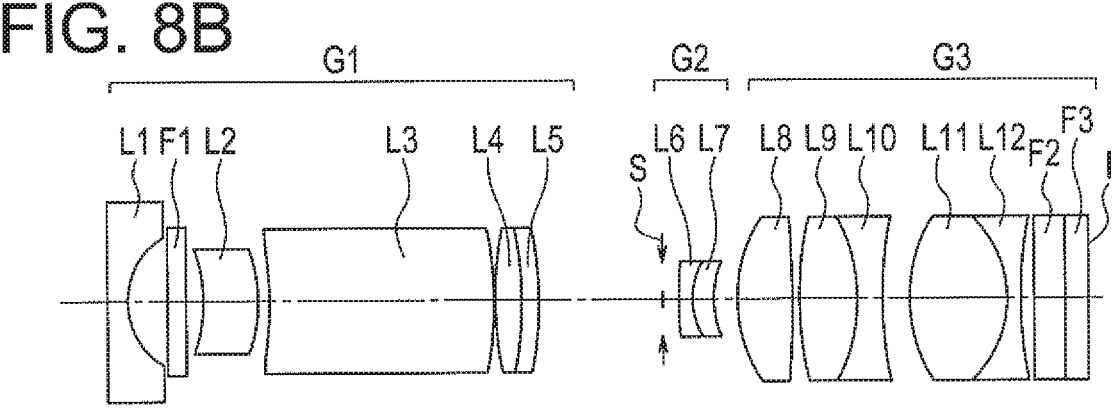

An objective optical system according to an example 4 will be described below. FIG. 8A and FIG. 8B are lens cross-sectional views of the objective optical system according to the example 4, where, FIG. 8A is a cross-sectional view in a normal observation state, and FIG. 8B is a cross-sectional view in a magnified observation state.

The objective optical system of the example 4, as shown in FIG. 8A and FIG. 8B, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a negative meniscus lens L3 having a convex surface directed toward the image side, a biconvex positive lens L4, and a negative meniscus lens L5 having a convex surface directed toward the image side. Here, the biconvex positive lens L4 and the negative meniscus lens L5 are cemented to form a cemented lens.

The second lens group G2 includes a negative meniscus lens L6 having a convex surface directed toward the object side and a positive meniscus lens L7 having a convex surface directed toward the object side. Here, the negative meniscus lens L6 and the positive meniscus lens L7 are cemented to forma cemented lens.

An aperture stop S is disposed between the first lens group G1 and the second lens group G2. More specifically, the aperture stop S is disposed nearest to object in the second lens group G2.

The third lens group G3 includes a biconvex positive lens L8, a biconvex positive lens L9, a biconcave negative lens L10, a biconvex positive lens L11, and a biconcave negative lens L12. Here, the biconvex positive lens L9 and the biconcave negative lens L10 are cemented to form a cemented lens. The biconvex positive lens L11 and the biconcave negative lens L12 are cemented to form a cemented lens.

A first sub-lens group SUB1 includes the biconvex positive lens L8, the biconvex positive lens L9, and the biconcave negative lens L10. A second sub-lens group SUB2 includes the biconvex positive lens L11 and the biconcave negative lens L12.

A plane parallel plate F1 is disposed on the image side of the planoconcave negative lens L1. A plane parallel plate F2 and a plane parallel plate F3 are disposed on the image side of the third lens group G3.

At a time of focusing, the second lens group G2 and the aperture stop S move integrally. At the time of focusing to an object point at a close distance from a state of being focused to an object point at a long distance, the second lens group G2 and the aperture stop S move toward the image side.

The objective optical system of the example 4 has the abovementioned basic arrangement, and also satisfies each of conditional expressions (1) to (12).

FIG. 9A, FIG. 9B, FIG. 9C, and FIG. 9D are aberration diagrams of a spherical aberration (SA), an astigmatism (AS), a distortion (DT), and a chromatic aberration of magnification (CC) respectively, in a normal observation state of the example 4. FIG. 9E, FIG. 9F, FIG. 9G, and FIG. 9H are aberration diagrams of a spherical aberration (SA), an astigmatism (AS), a distortion (DT), and a chromatic aberration of magnification (CC) respectively, in a magnified observation state of the example 4.

Example 5

Figure 10A:
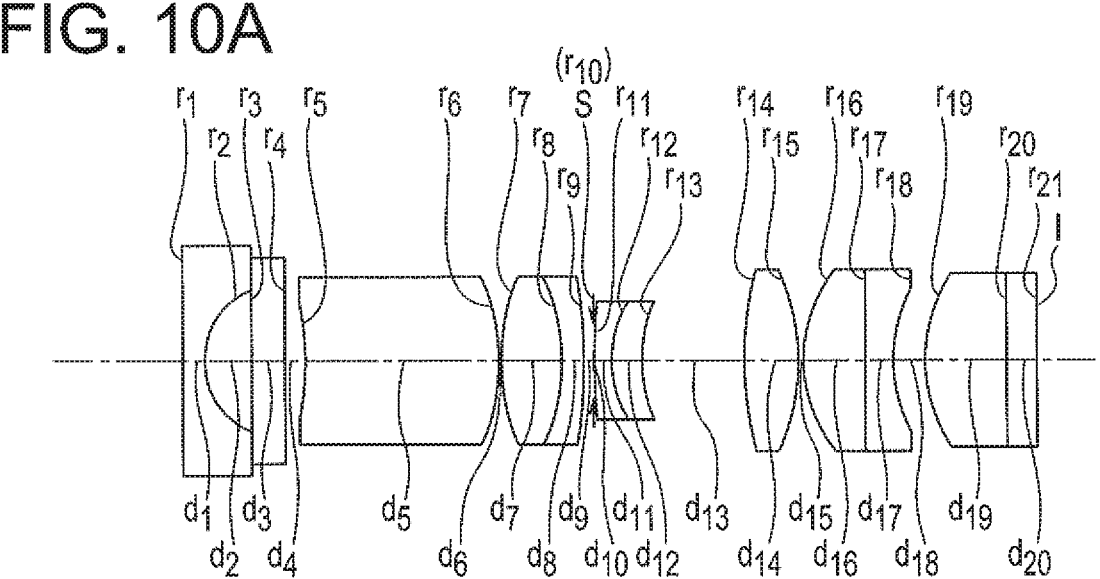
FIG. 10A and FIG. 10B are cross-sectional views of an objective optical system of an example 5.
Figure 10B:
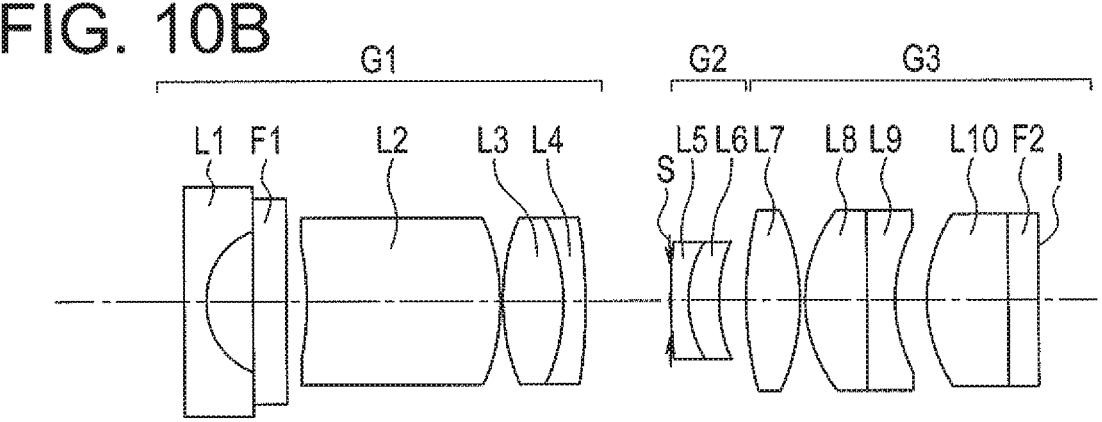

An objective optical system according to an example 5 will be described below. FIG. 10A and FIG. 10B are lens cross-sectional views of the objective optical system according to the example 5, where, FIG. 10A is a cross-sectional view in a normal observation state, and FIG. 10B is a cross-sectional view in a magnified observation state.

The objective optical system of the example 5, as shown in FIG. 10A and FIG. 10B, includes in order from an object side, a first lens group G1 having a positive refractive power, a second lens group G2 having a negative refractive power, and a third lens group G3 having a positive refractive power.

The first lens group G1 includes a planoconcave negative lens L1 of which an object side is a flat surface, a positive meniscus lens L2 having a convex surface directed toward an image side, a biconvex positive lens L3, and a negative meniscus lens L4 having a convex surface directed toward the image side. Here, the biconvex positive lens L3 and the negative meniscus lens L4 are cemented to form a cemented lens.

The second lens group G2 includes a negative meniscus lens L5 having a convex surface directed toward the object side and a positive meniscus lens L6 having a convex surface directed toward the object side. Here, the negative meniscus lens L5 and the positive meniscus lens L6 are cemented to form a cemented lens.

An aperture stop S is disposed between the first lens group G1 and the second lens group G2. More specifically, the aperture stop S is disposed nearest to object in the second lens group G2.

The third lens group G3 includes a biconvex positive lens L7, a biconvex positive lens L8, a biconcave negative lens L9, and a planoconvex positive lens L10 of which an image side is a flat surface. Here, the biconvex positive lens L8 and the biconcave negative lens L9 are cemented to form a cemented lens.

A first sub-lens group SUB1 includes the biconvex positive lens L7, the biconvex positive lens L8, and the biconcave negative lens L9. A second sub-lens group SUB2 includes the planoconvex positive lens L10.

A plane parallel plate F1 is disposed on the image side of the planoconcave negative lens L1. A plane parallel plate F2 is disposed on the image side of the third lens group G3.

At a time of focusing, the second lens group G2 and the aperture stop S move integrally. At the time of focusing to an object point at a close distance from a state of being focused to an object point at a long distance, the second lens group G2 and the aperture stop S move toward the image side.

The objective optical system of the example 5 has the abovementioned basic arrangement, and also satisfies each of conditional expressions (1) to (12).

FIG. 11A, FIG. 11B, FIG. 11C, and FIG. 11D are aberration diagrams of a spherical aberration (SA), an astigmatism (AS), a distortion (DT), and a chromatic aberration of magnification (CC) respectively, in a normal observation state of the example 5. FIG. 11E, FIG. 11F, FIG. 11G, and FIG. 11H are aberration diagrams of a spherical aberration (SA), an astigmatism (AS), a distortion (DT), and a chromatic aberration of magnification (CC) respectively, in a magnified observation state of the example 5.

Numerical data of each example described above is shown below. In Surface data, r denotes radius of curvature of each lens surface, d denotes a distance between respective lens surfaces, ne denotes a refractive index of each lens for e-line, vd denotes an Abbe number for each lens.

In Various data, f denotes a focal length in e-line, Fno denotes an F number, ω denotes a half angle of view, IH denotes an image height, OBJ denotes an object distance. In the close observation state, it is possible to carry out the magnified observation.

Example 1

Unit mm

Surface data

| Surface no. | r | d | ne | vd |
|---|---|---|---|---|
| 1 | ∞ | 0.380 | 1.88815 | 40.76 |
| 2 | 1.4587 | 0.799 | | |
| 3 | ∞ | 0.600 | 1.52300 | 65.13 |
| 4 | ∞ | 0.207 | | |
| 5 | −18.6140 | 5.430 | 1.75453 | 35.33 |
| 6 | −4.1342 | 0.035 | | |
| 7 | 6.6210 | 0.602 | 1.77621 | 49.60 |
| 8 | −7.1500 | 0.305 | 1.93429 | 18.90 |
| 9 | ∞ | Variable | | |
| 10(Stop) | ∞ | 0.018 | | |
| 11 | 16.0613 | 0.383 | 1.48915 | 70.23 |
| 12 | 1.8136 | 0.718 | 1.59667 | 35.31 |
| 13 | 2.3792 | Variable | | |
| 14 | 3.1450 | 1.187 | 1.48915 | 70.23 |
| 15 | −25.8393 | 0.470 | | |
| 16 | 2.5943 | 1.393 | 1.49846 | 81.54 |
| 17 | −3.2345 | 0.478 | 1.93429 | 18.90 |
| 18 | −10.6398 | 1.042 | | |
| 19 | ∞ | 0.500 | 1.51825 | 64.14 |
| 20 | ∞ | 0.500 | 1.51825 | 64.14 |
| 21(Image pickup surface) | ∞ | | | |

Various data

| | Normal observation state | Close observation state |
|---|---|---|
| f | 1.078 | 1.273 |
| Fno | 2.97 | 3.07 |
| OBJ | 25.0 | 2.4 |
| d9 | 0.161 | 1.756 |
| d13 | 1.850 | 0.255 |
| 2ω | 160.5 | |
| IH | 1.0 | |

Example 2

Unit mm

Surface data

| Surface no. | r | d | ne | vd |
|---|---|---|---|---|
| 1 | ∞ | 0.380 | 1.88815 | 40.76 |
| 2 | 1.5663 | 1.000 | | |
| 3 | ∞ | 0.480 | 1.52300 | 65.13 |
| 4 | ∞ | 0.123 | | |
| 5 | −8.8662 | 1.643 | 1.51825 | 64.14 |
| 6 | −2.4040 | 2.890 | 1.79192 | 25.68 |
| 7 | −4.7427 | 0.032 | | |
| 8 | 6.8671 | 0.612 | 1.74678 | 49.34 |
| 9 | −7.1946 | 0.239 | 1.93429 | 18.90 |
| 10 | −12.1150 | Variable | | |
| 11(Stop) | ∞ | 0.016 | | |
| 12 | 8.6769 | 0.319 | 1.48915 | 70.23 |
| 13 | 2.0266 | 0.363 | 1.59667 | 35.31 |
| 14 | 2.7096 | Variable | | |
| 15 | 3.8880 | 1.018 | 1.49846 | 81.54 |
| 16 | 338.4541 | 0.522 | | |
| 17 | 4.7770 | 1.262 | 1.77621 | 49.60 |
| 18 | −5.0132 | 0.478 | 1.93429 | 18.90 |
| 19 | 11.7885 | 0.032 | | |
| 20 | 3.5786 | 1.805 | 1.48915 | 70.23 |
| 21 | −3.1896 | 0.287 | 1.70442 | 30.13 |
| 22 | −21.0502 | 0.274 | | |
| 23 | ∞ | 0.880 | 1.51825 | 64.14 |
| 24(Image pickup surface) | ∞ | | | |

Various data

| | Normal observation state | Close observation state |
|---|---|---|
| f | 1.025 | 1.195 |
| Fno | 2.78 | 2.80 |
| OBJ | 24.0 | 2.30 |
| d10 | 0.175 | 2.185 |
| d14 | 2.432 | 0.422 |
| 2ω | 160.5 | |
| IH | 1.0 | |

Example 3

Unit mm

Surface data

| Surface no. | r | d | ne | vd |
|---|---|---|---|---|
| 1 | ∞ | 0.380 | 1.88815 | 40.76 |
| 2 | 1.7011 | 1.720 | | |
| 3 | ∞ | 0.500 | 1.52300 | 65.13 |
| 4 | ∞ | 0.426 | | |
| 5 | −5.5510 | 4.268 | 1.80642 | 34.97 |
| 6 | −1.7758 | 0.319 | 1.77621 | 49.60 |
| 7 | −6.1467 | 0.064 | | |
| 8 | 8.6816 | 0.955 | 1.74678 | 49.34 |
| 9 | −3.1980 | 0.367 | 1.93429 | 18.90 |
| 10 | −9.3464 | Variable | | |
| 11(Stop) | ∞ | 0.020 | | |
| 12 | 4.7361 | 0.367 | 1.48915 | 70.23 |
| 13 | 1.7836 | 0.510 | 1.59667 | 35.31 |
| 14 | 2.3291 | Variable | | |

-continued

Unit mm

| | | | | |
|---|---|---|---|---|
| 15 | 5.0948 | 1.037 | 1.49846 | 81.54 |
| 16 | −21.8928 | 0.518 | | |
| 17 | 3.7908 | 1.435 | 1.53947 | 74.70 |
| 18 | −8.4992 | 0.032 | | |
| 19 | 72.4876 | 1.276 | 1.77621 | 49.60 |
| 20 | −3.0891 | 0.478 | 1.93429 | 18.90 |
| 21 | 17.8264 | 0.827 | | |
| 22 | ∞ | 0.550 | 1.51825 | 64.14 |
| 23(Image pickup surface) | ∞ | | | |

Various data

| | Normal observation state | Close observation state |
|---|---|---|
| f | 1.032 | 1.148 |
| Fno | 3.52 | 3.39 |
| OBJ | 27.5 | 3.39 |
| d10 | 0.161 | 2.586 |
| d14 | 2.691 | 0.266 |
| 2ω | 159.9 | |
| IH | 1.0 | |

Example 4

Unit mm

Surface data

| Surface no. | r | d | ne | vd |
|---|---|---|---|---|
| 1 | ∞ | 0.380 | 1.88815 | 40.76 |
| 2 | 1.4628 | 0.788 | | |
| 3 | ∞ | 0.400 | 1.52300 | 65.13 |
| 4 | ∞ | 0.312 | | |
| 5 | −4.4644 | 1.099 | 1.51825 | 64.14 |
| 6 | −3.5574 | 0.241 | | |
| 7 | −6.0332 | 4.489 | 1.79192 | 25.68 |
| 8 | −7.8612 | 0.037 | | |
| 9 | 9.3035 | 0.545 | 1.74678 | 49.34 |
| 10 | −6.9466 | 0.311 | 1.93429 | 18.90 |
| 11 | −9.4719 | Variable | | |
| 12(Stop) | ∞ | 0.319 | | |
| 13 | 7.6703 | 0.319 | 1.48915 | 70.23 |
| 14 | 1.8775 | 0.410 | 1.59667 | 35.31 |
| 15 | 2.7199 | Variable | | |
| 16 | 2.9238 | 1.100 | 1.49846 | 81.54 |
| 17 | −17.0596 | 0.153 | | |
| 18 | 7.1193 | 1.201 | 1.48915 | 70.23 |
| 19 | −2.9030 | 0.478 | 1.93429 | 18.90 |
| 20 | 19.7236 | 0.511 | | |
| 21 | 3.0590 | 1.960 | 1.70442 | 30.13 |
| 22 | −2.1384 | 0.283 | 1.77621 | 49.60 |
| 23 | 15.9445 | 0.266 | | |
| 24 | ∞ | 0.630 | 1.51825 | 64.14 |
| 25 | ∞ | 0.470 | 1.51825 | 64.14 |
| 26(Image pickup surface) | ∞ | | | |

Various data

| | Normal observation state | Close observation state |
|---|---|---|
| f | 1.071 | 1.235 |
| Fno | 3.80 | 3.83 |
| OBJ | 25.5 | 2.40 |
| d11 | 0.163 | 2.459 |
| d15 | 2.757 | 0.461 |
| 2ω | 149.6 | |
| IH | 1.0 | |

Example 5

Unit mm

Surface data

| Surface no. | r | d | ne | vd |
|---|---|---|---|---|
| 1 | ∞ | 0.390 | 1.88815 | 40.76 |
| 2 | 1.4328 | 0.844 | | |
| 3 | ∞ | 0.650 | 1.52300 | 65.13 |
| 4 | ∞ | 0.355 | | |
| 5 | −5.0442 | 3.505 | 1.75453 | 35.33 |
| 6 | −3.4362 | 0.033 | | |
| 7 | 4.0546 | 1.080 | 1.48915 | 70.23 |
| 8 | −3.5697 | 0.395 | 1.93429 | 18.90 |
| 9 | −6.4779 | Variable | | |
| 10(Stop) | ∞ | 0.020 | | |
| 11 | 11.8662 | 0.329 | 1.48915 | 70.23 |
| 12 | 1.9770 | 0.536 | 1.59667 | 35.31 |
| 13 | 2.2723 | Variable | | |
| 14 | 6.4662 | 0.992 | 1.53947 | 74.70 |
| 15 | −3.7887 | 0.107 | | |
| 16 | 2.4798 | 1.132 | 1.48915 | 70.23 |
| 17 | −61.1928 | 0.493 | 1.93429 | 18.90 |
| 18 | 3.0984 | 0.565 | | |
| 19 | 2.7725 | 1.480 | 1.51825 | 64.14 |
| 20 | ∞ | 0.575 | 1.50000 | 60.00 |
| 21(Image pickup surface) | ∞ | | | |

Various data

| | Normal observation state | Close observation state |
|---|---|---|
| f | 1.046 | 1.207 |
| Fno | 3.00 | 3.05 |
| OBJ | 26.3 | 2.45 |
| d9 | 0.165 | 1.475 |
| d13 | 1.800 | 0.498 |
| 2ω | 144.0 | |
| IH | 1.0 | |

The values of conditional expressions (1) to (12) from the first example to the fifth example are shown below.

| Conditional expression | Example1 | Example2 | Example3 |
|---|---|---|---|
| (1)fp/f | 1.819 | 2.116 | 1.940 |
| (2)tt/f | 0.436 | 0.509 | 0.502 |
| (3)fG2/f | −6.207 | −9.445 | −13.023 |
| (4)fG3SUB1/fG3SUB2 | 0.882 | 1.270 | 1.134 |
| (5)fG2/fG1 | −2.821 | −3.618 | −4.671 |
| (6)fG2/fG3 | −1.981 | −2.585 | −3.361 |
| (7)fG3/fG1 | 1.424 | 1.400 | 1.390 |
| (8)(t12 + t23)/f | 1.882 | 2.559 | 2.782 |
| (9)fL1/fG1 | −0.693 | −0.659 | −0.665 |
| (10)rG3SUB2F/f | 2.407 | 4.660 | 3.672 |
| (11)fG3SUB2F/f | 4.829 | 6.005 | 6.806 |
| (12)fG1CL/rG1CL | −1.457 | −0.885 | −2.505 |

| Conditional expression | Example4 | Example5 |
|---|---|---|
| (1)fp/f | 1.853 | 1.327 |
| (2)tt/f | 0.477 | 0.540 |
| (3)fG2/f | −10.447 | −6.103 |
| (4)fG3SUB1/fG3SUB2 | 1.345 | 0.780 |
| (5)fG2/fG1 | −3.914 | −2.935 |
| (6)fG2/fG3 | −2.602 | −1.985 |
| (7)fG3/fG1 | 1.504 | 1.479 |
| (8)(t12 + t23)/f | 3.023 | 1.906 |

-continued

| | | |
|---|---|---|
| (9) fL1/fG1 | −0.576 | −0.742 |
| (10) rG3SUB2F/f | 2.855 | 2.651 |
| (11) fG3SUB2F/f | 4.053 | 5.116 |
| (12) fG1CL/rG1CL | −0.964 | −2.026 |

Various embodiments of the present invention were described above. However, the present invention is not restricted to the embodiments described above, and embodiments in which arrangements of the embodiments described above are combined appropriately without departing from the scope of the invention are also within the scope of the present invention.

(Note)

An invention of the following arrangement is derived from the examples described above.

(Appended Mode 1)

An objective optical system, comprising in order from an object side:

a first lens group having a positive refractive power;

a second lens group having a negative refractive power; and a third lens group having a positive refractive power, wherein focusing is carried out by moving the second lens group, and the third lens group includes at least a positive lens and a cemented lens, and the cemented lens in the third lens group includes a positive lens and a negative lens, and a first sub-lens group in the third lens group is positioned on the object side of a predetermined air space, and a second sub-lens group in the third lens group is positioned on an image side of the predetermined air space, and the predetermined air space is the maximum air space among the air spaces in the third lens group, and the following conditional expressions (1) and (2) are satisfied:

$$1.21 < fp/f < 2.42 \qquad (1), \text{ and}$$

$$0.35 < tt/f < 0.6 \qquad (2)$$

where, fp denotes a combined focal length from the first lens group up to the first sub-lens group, f denotes a focal length of the overall objective optical system at the time of focusing to an object point at a long distance, and tt denotes the predetermined air space.

(Appended Mode 2)

The objective optical system according to appended mode 1, wherein the following conditional expression (3) is satisfied:

$$15 < fG2/f < -5 \qquad (3)$$

where, fG2 denotes a focal length of the second lens group, and f denotes the focal length of the overall objective optical system at the time of focusing to an object point at a long distance.

(Appended Mode 3)

The objective optical system according to one of appended modes 1 and 2, wherein the following conditional expression (4) is satisfied:

$$0.7 < fG3SUB1/fG3SUB2 < 1.4 \qquad (4)$$

where, fG3SUB1 denotes a focal length of the first sub-lens group, and fG3SUB2 denotes a focal length of the second sub-lens group.

(Appended Mode 4)

The objective optical system according to any one of appended modes 1 to 3, wherein any one of the following conditional expressions (5) to (9) is satisfied:

$$-6 < fG2/fG1 < -2 \qquad (5),$$

$$-7.6 < fG2/fG3 < -2.4 \qquad (6),$$

$$1.0 < fG3/fG1 < 2.0 \qquad (7),$$

$$1.4 < (t12+t23)/f < 3.2 \qquad (8), \text{ and}$$

$$-0.8 < fL1/fG1 < -0.5 \qquad (9)$$

where, fG1 denotes a focal length of the first lens group, fG2 denotes the focal length of the second lens group, fG3 denotes a focal length of the third lens group, t12 denotes a distance between the first lens group and the second lens group at the time of focusing to an object point at a long distance, t23 denotes a distance between the second lens group and the third lens group at the time of focusing to an object point at a long distance, f denotes the focal length of the overall objective optical system at the time of focusing to an object point at a long distance, and fL1 denotes a focal length of the first lens.

(Appended Mode 5)

The objective optical system according to any one of appended modes 1 to 4, wherein the following conditional expression (10) is satisfied:

$$1.8 < rG3SUB2F/f < 5.2 \qquad (10)$$

where, rG3SUB2F denotes a radius of curvature of a lens surface positioned nearest to object of the second sub-lens group, and f denotes the focal length of the overall objective optical system at the time of focusing to an object point at a long distance.

(Appended Mode 6)

The objective optical system according to any one of appended modes 1 to 5, wherein the third lens group includes in order form the object side, a positive lens and a cemented lens.

(Appended Mode 7)

The objective optical system according to any one of appended modes 1 to 5, wherein the third lens group further includes another positive lens, and the third lens group includes in order from the object side, a positive lens, a cemented lens, and another positive lens.

(Appended Mode 8)

The objective optical system according to any one of appended modes 1 to 5, wherein the third lens group further includes another cemented lens, and the another cemented lens includes a positive lens and a negative lens, and the third lens group includes in order from the object side, a positive lens, a cemented lens, and another cemented lens.

(Appended Mode 9)

The objective optical system according to any one of appended modes 1 to 8, wherein the following conditional expression (11) is satisfied:

$$4.0 < fG3SUB2F/f < 6.5 \qquad (11)$$

where, fG3SUB2F denotes a focal length of a predetermined lens surface, and f denotes the focal length of the overall objective optical system at the time of focusing to an object point at a long distance, and the predetermined lens surface is a lens surface positioned nearest to object of the second sub-lens group.

(Appended Mode 10)

The objective optical system according to any one of appended modes 1 to 9, wherein a lens positioned nearest to image in the third lens group is a planoconvex lens, and an object-side surface of the planoconvex lens is a surface convex toward the object side.

(Appended Mode 11)

The objective optical system according to any one of appended modes 1 to 10, wherein the following conditional expression (12) is satisfied:

$$3.0 < fG1CL/rG1CL < -0.7 \qquad (12)$$

where, fG1CL denotes a focal length of the predetermined cemented lens, and rG1CL denotes a radius of curvature of a cemented surface of the predetermined cemented lens.

(Appended Mode 12)

The objective optical system according to any one of appended modes 1 to 11, wherein the first lens group includes in order from an object side, at least a planoconcave lens having a concave surface directed toward the image side, a positive meniscus lens having a convex surface directed toward the image side, a biconvex lens, and a negative meniscus lens having a convex surface directed toward the image side, and the biconvex lens and the negative meniscus lens having the convex surface directed toward the image side are cemented.

(Appended Mode 13)

The objective optical system according to any one of appended modes 1 to 11, wherein the first lens group includes in order from the object side, at least a planoconcave lens having a concave surface directed toward the image side, a positive meniscus lens having a convex surface directed toward the image side, a negative meniscus lens having a convex surface directed toward the image side, a biconvex lens, and a negative meniscus lens having a convex surface directed toward the image side, and the positive meniscus lens having the convex surface directed toward the image side and the negative meniscus lens having the convex surface directed toward the image side are cemented, and the biconvex lens and the negative meniscus lens having the convex surface directed toward the image side are cemented.

According to the objective optical system of the present embodiment, it is possible to provide an objective optical system which is not susceptible to have an effect due to various errors, and in which various aberrations are corrected favorably.

As described above, the present invention is useful for an objective optical system which is not susceptible to have an effect due to various errors, and in which various aberrations are corrected favorably.

What is claimed is:

1. An objective optical system, comprising in order from an object side:

a first lens group having a positive refractive power;

a second lens group having a negative refractive power; and a third lens group having a positive refractive power, wherein:

focusing is carried out by moving the second lens group, the third lens group includes at least a positive lens and a cemented lens, the cemented lens in the third lens group includes a positive lens and a negative lens, a first sub-lens group in the third lens group includes a lens positioned on the object side of a predetermined air space, a second sub-lens group in the third lens group includes a lens positioned on an image side of the predetermined air space, the predetermined air space is the maximum air space among the any air spaces in the third lens group, and the following conditional expressions (1) and (2) are satisfied:

$$1.21 < fp/f < 2.42 \qquad (1), \text{ and}$$

$$0.35 < tt/f < 0.6 \qquad (2)$$

where, fp denotes a combined focal length of a part of the objective optical system from the first lens group to the first sub-lens group at a time of focusing to an object point at a long distance, f denotes a focal length of the overall objective optical system at the time of focusing to an object point at a long distance, and tt denotes the predetermined air space.

2. The objective optical system according to claim 1, wherein the following conditional expression (3) is satisfied:

$$-15 < fG2/f < -5 \qquad (3)$$

where, fG2 denotes a focal length of the second lens group, and f denotes the focal length of the overall objective optical system at the time of focusing to an object point at a long distance.

3. The objective optical system according to claim 1, wherein the following conditional expression (4) is satisfied:

$$0.7 < fG3SUB1/fG3SUB2 < 1.4 \qquad (4)$$

where, fG3SUB1 denotes a focal length of the first sub-lens group, and fG3SUB2 denotes a focal length of the second sub-lens group.

4. The objective optical system according to claim 1, wherein the first sub-lens group includes one of the positive lens and the cemented lens.

5. An image pick-up apparatus comprising:

the objective optical system according to claim 1.

6. An endoscope comprising:

the objective optical system according to claim 1.

* * * * *